United States Patent
Lintereur et al.

(10) Patent No.: US 12,233,238 B2
(45) Date of Patent: Feb. 25, 2025

(54) DIABETES THERAPY BASED ON DETERMINATION OF FOOD ITEM

(71) Applicant: Medtronic MiniMed, Inc., Northridge, CA (US)

(72) Inventors: Louis J. Lintereur, Boise, ID (US); Cleveland Rayford, II, Valencia, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 886 days.

(21) Appl. No.: 17/090,938

(22) Filed: Nov. 6, 2020

(65) Prior Publication Data

US 2022/0143314 A1    May 12, 2022

(51) Int. Cl.
*G16H 20/60*    (2018.01)
*A61M 5/172*    (2006.01)
*G06N 20/00*    (2019.01)

(52) U.S. Cl.
CPC ............. *A61M 5/172* (2013.01); *G06N 20/00* (2019.01); *G16H 20/60* (2018.01);
(Continued)

(58) Field of Classification Search
None
See application file for complete search history.

(56) References Cited

U.S. PATENT DOCUMENTS

2013/0317316 A1* 11/2013 Kandeel ................. G16H 50/50
                                                          600/300
2017/0173262 A1   6/2017 Veltz
(Continued)

FOREIGN PATENT DOCUMENTS

DE    102013008594 A1 * 11/2014 ......... G06F 19/3456
WO    WO-2021167675 A1 *  8/2021 ........... A61B 5/0004

OTHER PUBLICATIONS

Jyoti M. Benni & Paragouda A. Patil, Non-diabetic clinical applications of insulin, 27 Journal of Basic and Clinical Physiology and Pharmacology, 445-456 (2016), https://www.degruyter.com/document/doi/10.1515/jbcpp-2015-0101/html (last visited Feb. 23, 2024) (Year: 2016).*

(Continued)

*Primary Examiner* — Jonathon A. Szumny
*Assistant Examiner* — Nicholas Akogyeram, II
(74) *Attorney, Agent, or Firm* — Weaver Austin Villeneuve & Sampson LLP

(57) ABSTRACT

Devices, systems, and techniques for guiding therapy delivery to a diabetes patient is described. Some devices, systems, and techniques proactively monitor the patient's food consumption and (if needed) adapt the patient's diabetes therapy accordingly. In one example, a system comprises one or more sensors configured to capture a representation of the object, and processing circuitry configured to determine data corresponding to the representation of the object, wherein the data comprises information identifying the object as a particular food item; generate food item information based on the information identifying the object as the particular food item, wherein the food item information comprises at least one of nutrition information or volume information of the particular food item, generate therapy information for the patient based on the food item information, and output content indicative of at least one of the therapy information or the food item information.

19 Claims, 7 Drawing Sheets

(52) U.S. Cl.
CPC ............... *A61M 2205/3306* (2013.01); *A61M 2205/502* (2013.01); *A61M 2205/52* (2013.01)

(56) References Cited

U.S. PATENT DOCUMENTS

| | | | | |
|---|---|---|---|---|
| 2017/0323481 | A1* | 11/2017 | Tran | H04N 23/611 |
| 2018/0204111 | A1* | 7/2018 | Zadeh | G06V 10/764 |
| 2019/0000382 | A1* | 1/2019 | Fitzpatrick | G16Z 99/00 |
| 2019/0341149 | A1* | 11/2019 | Chiu | G16H 20/30 |
| 2020/0090417 | A1* | 3/2020 | Schloter | G06T 7/33 |
| 2020/0135320 | A1* | 4/2020 | Vleugels | G16H 20/17 |
| 2021/0260287 | A1* | 8/2021 | Kamath | G16H 50/20 |

OTHER PUBLICATIONS

Sediqeh Samadi et al., Automatic Detection and Estimation of Unannounced Meals for Multivariable Artificial Pancreas System, Diabetes Technology & Therapeutics 20, 235-246 (2018), https://www.liebertpub.com/doi/epub/10.1089/dia.2017.0364 (last visited Oct. 4, 2024) (Year: 2018).*

"Apple Might Debut with a LIDAR Sensor in New Smartphones," from ACE electroncisforu.com, accessed from https://ace.electronicsforu.com/buzz/new-products/smartphones/apple-might-debut-with-a-LIDAR-sensor-in-new-smartphones/, dated Apr. 6, 2020, 2 pp.

"Matterport Brings 3D Capture to the iPhone," by PR Newswire, provided by Matterport, accessed from https://www.prnewswire.com/news-releases/matterport-brings-3d-capture-to-the-iphone-301051911.html, dated May 4, 2020, 4 pp.

de With S., "LIDAR: Peek Into the Future With iPad Pro," from HALIDE, accessed from https://blog.halide.cam/LIDAR-peek-into-the-future-with-ipad-pro-11d38910e9f8, dated Apr. 15, 2020, 18 pp.

Gartenberg, C., "The new iPad Pro's LIDAR sensor is an AR hardware solution in search of software—Is LIDAR really the missing piece of the puzzle," from The Verge, accessed from https://www.theverge.com/2020/3/19/21185200/apple-ipad-pro-LIDAR-sensor-ar-hardware-solution-software-apps-augmented reality, dated Mar. 19, 2020, 3 pp.

Goodwin, K., "Thermal Imaging—Best Thermal Imaging Apps (for Android and iOS) 2020," from Thermogears, accessed from https://thermogears.com/best-thermal-imaging-apps-android-ios/, dated Oct. 7, 2020, 7 pp.

Hardwick, T., "Report: Apple's New 'World-Facing' 3D Camera Coming to at Least One iPhone This Year," from MacRumors, accessed from https://www.macrumors.com/2020/03/12/apple-new-world-facing-3d-camera-2020-phone/, dated Mar. 12, 2020, 10 pp.

IEEE 802.11ad, "IEEE Standard for Information Technology—Telecommunications and Information Exchange Between Systems—Local and Metropolitan Area Networks—Specific Requirements—Part 11: Wireless LAN Medium Access Control (MAC) and Physical Layer (PHY) Specifications—Amendment 3: Enhancements for Very High Throughput in the 60 GHz Band", IEEE Computer Society, Dec. 28, 2012, 628 pp.

Knight, J, "LiDAR vs. 3D ToF Sensors—How Apple Is Making AR Better for Smartphones," from Gadget Hacks Shop, accessed from https://ios.gadgethacks.com/news/lidar-vs-3d-tof-sensors-apple-is-making-ar-better-for-smartphones-0280778/, dated Mar. 31, 2020, 7 pp.

MacRumors Staff, "iPhone 12—Everything we know about Apple's just-announced mainstream 2020 iPhones, the iPhone 12 and the iPhone 12 minim. iPhone 12 available now, iPhone 12 mni coming in November," from MacRumors, accessed from https://www.macrumors.com/roundup/iphone-12/, dated Oct. 26, 2020, 47 pp.

Porter, J., "Go read this analysis of what the iPad Pro's LIDAR sensor is capable of—Less photography, more augmented reality," from The Verge, accessed from https://www.theverge.com/2020/4/16/21223626/ipad-pro-halide-camera-LIDAR-sensor-augmented-reality-scanning, dated Apr. 16, 2020, 2 pp.

Response to Extended Search Report dated Mar. 30, 2022, from counterpart European Application No. 21206600.5, filed Nov. 9, 2022, 21 pp.

Anthimopoulos et al., "A Food Recognition System for Diabetic Patients Based on an Optimized Bag-of-Features Model", IEEE Journal of Biomedical and Health Informatics, vol. 18, No. 4, Jul. 2014, pp. 1261-1271.

Extended Search Report from counterpart European Application No. 21206600.5, dated Mar. 30, 2022, 11 pp.

Wesley et al., "Current Developments in Digital Quantitative Volume Estimation for the Optimisation of Dietary Assessment", Nutrients, vol. 12, No. 4, Apr. 22, 2020, 23 pp.

* cited by examiner

DIABETES THERAPY BASED ON DETERMINATION OF FOOD ITEM

TECHNICAL FIELD

The disclosure relates to medical systems and, more particularly, to medical systems for therapy for diabetes.

BACKGROUND

A patient with diabetes receives insulin from a pump or injection device to control the glucose level in his or her bloodstream. Naturally produced insulin may not control the glucose level in the bloodstream of a diabetes patient due to insufficient production of insulin and/or due to insulin resistance. To control the glucose level, a patient's therapy routine may include dosages of basal insulin and bolus insulin. Basal insulin, also called background insulin, tends to keep blood glucose levels at consistent levels during periods of fasting and is a long acting or intermediate acting insulin. Bolus insulin may be taken specifically at or near mealtimes or other times where there may be a relatively fast change in glucose level, and may therefore serve as a short acting or rapid acting form of insulin dosage.

SUMMARY

Devices, systems, and techniques for managing glucose level in a patient are described. In various examples, one or more devices provides sensor-based proactive monitoring and control of a patient's food consumption (including consumption of beverages). A patient device configured to deliver an appropriate diabetes therapy to the patient may also protect that patient from being administered an improper and/or ineffective treatment, for example, because of certain food item(s) that the patient consumed. One or more processors (e.g., in a patient device such as a pen for insulin delivery, a pump for insulin delivery, or another device; in a mobile or desktop computing device; and/or in one or more servers in a network cloud) may be configured to detect a meal event and/or determine which food items are to be consumed during the detected meal event. In addition, the one or more processors may generate food item information including information indicating how consuming any of these food items may affect delivery of the patient's diabetes therapy.

In at least one example, the one or more processors may compute a carbohydrate count, based on the generated food item information, for a food item. The one or more processors may determine, based on the carbohydrate count, that there will be an increase in the glucose level in the patient. If the patient's diabetes therapy is insufficient to compensate for the increase in the glucose level or may overcompensate for the increase in the glucose level, the one or more processors may communicate a message to a device being viewed by the patient's caregiver. The message may include data for display on the device's electronic display and/or an instruction to apply an amount or type of diabetes treatment (e.g., insulin). In some examples, the one or more processors may output instructions to an insulin delivery device (e.g., insulin pump and/or injection device) indicating the amount of insulin to deliver.

In one example, the disclosure describes a system comprising one or more sensors configured to capture a representation of the object, and processing circuitry configured to determine data corresponding to the representation of the object, wherein the data comprises information identifying the object as a particular food item; generate food item information based on the information identifying the object as the particular food item, wherein the food item information comprises at least one of nutrition information or volume information of the particular food item, generate therapy information for the patient based on the food item information, and output content indicative of at least one of the therapy information or the food item information.

The details of one or more aspects of the disclosure are set forth in the accompanying drawings and the description below. Other features, objects, and advantages of this disclosure will be apparent from the description and drawings, and from the claims.

DETAILED DESCRIPTION

Figure 1:
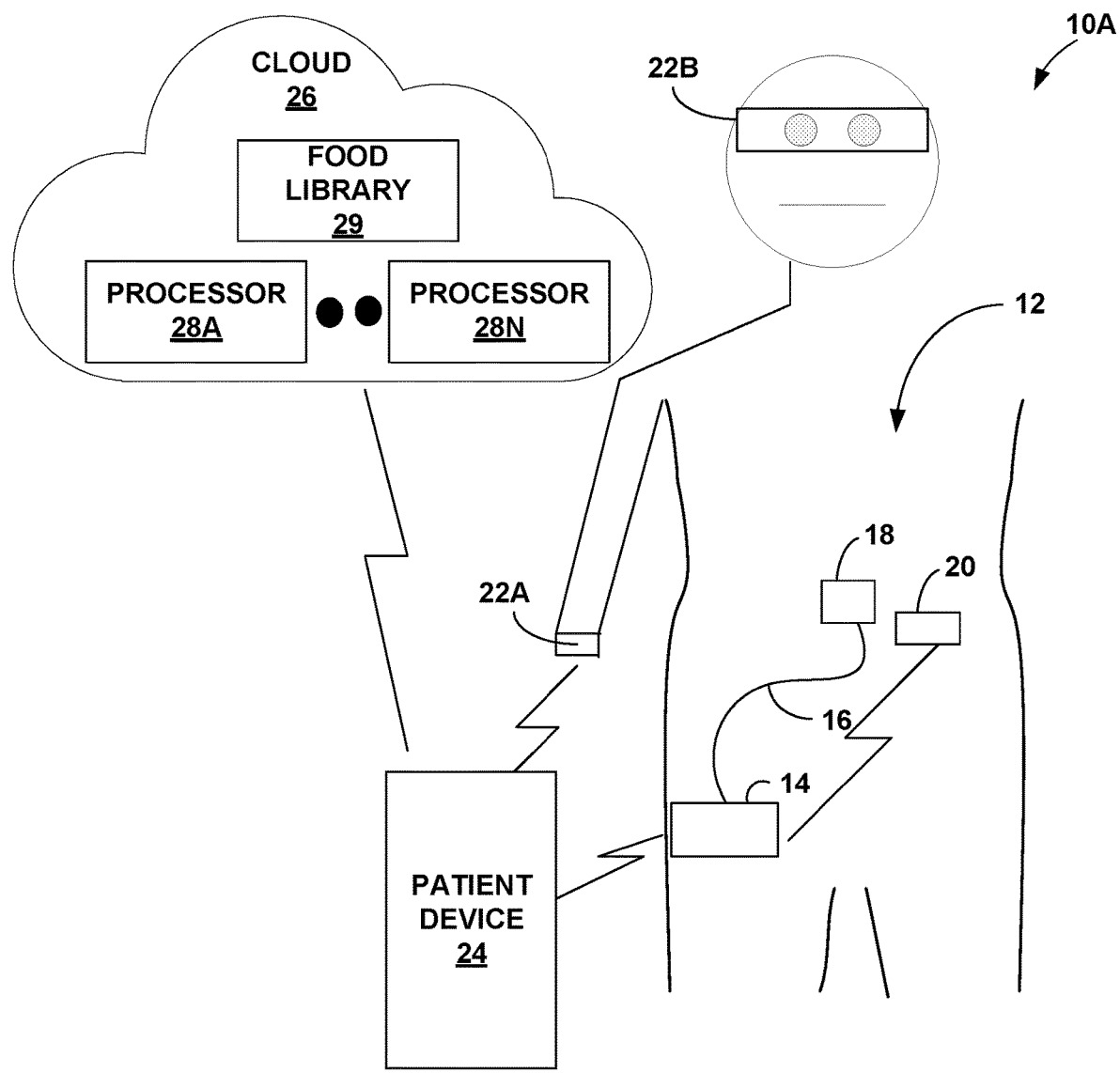
FIG. 1 is a block diagram illustrating an example system for delivering or guiding therapy dosage, in accordance with one or more examples described in this disclosure.

Devices, systems, and techniques for managing glucose level in a patient are described in this disclosure. Some devices, systems, and techniques enable glucose management by proactively monitoring patient food consumption. For any patient especially diabetic patients, maintaining good health in general requires maintaining a healthy blood sugar level within a target range. In the present disclosure, blood sugar level and glucose level are synonymous and may be described herein interchangeably. Having low blood sugar (e.g., hypoglycemia) or high blood sugar (e.g., fasting hyperglycemia and postprandial hyperglycemia) may result in long-term, serious health problems, such as heart disease, vision loss, and kidney disease. Hypoglycemia may be detected if a blood sugar level falls below 70 mg/dL. Fasting hyperglycemia may be detected if a blood sugar rises above 130 mg/dL after not eating or drinking for at least 8 hours. Postprandial or after-meal hyperglycemia may be detected if a blood sugar level rises above 180 mg/dL 2 hours after eating. People without diabetes rarely have blood sugar levels over 140 mg/dL after a meal.

If the patient is able to maintain their blood sugar level within a target range as much as possible, such maintenance prevents or at least postpones any of these long-term, serious health problems and improves their energy and mood. Patients may develop low or inadequate blood sugar levels for a number of reasons, including missing a meal, inaccurate dosing resulting in too much insulin in the body, side-effects from other diabetes medicines, exercising more than normal, and drinking certain beverages (e.g., certain alcoholic beverages). Patients may develop high blood sugar levels for a number of reasons, including skipping or forgetting a dose of insulin or any other glucose-lowering medicine, eating too many grams of carbohydrates in general and/or relative to an actual amount of insulin in the body, having an infection or an illness, and either becoming inactive or, conversely, engaging in strenuous physical activity—especially when blood sugar levels are high and insulin levels are low. Hence, the patient's diet has a major influence on that patient's glucose level and eating a healthful diet of food portions and plenty of fruit and vegetables, at regular times and without skipping meals, should be a major component of the patient's glucose management.

For at least these reasons, the patient may benefit by having nutrition information and/or volume information for each food item prior to consumption. For example, carbohydrates consumed from a meal may increase the glucose level in a patient, and insulin may counteract the increase the glucose level. If an assumption of the amount of carbohydrates, or possibly other macronutrients, is incorrect, then too much insulin may be delivered, causing low glucose level, or not enough insulin may be delivered, causing high glucose level.

By knowing ahead of time whether certain food item(s), if consumed, may cause high blood sugar, the patient may decide to substitute the food item, eat a smaller portion, or avoid the food item altogether. Most health professionals recommend that the patient control their food portions and nutrition intake (for example, using the plate method: fill half your plate with non-starchy vegetables, a quarter with lean protein, and a quarter with a grain or starchy food). The patient should select foods that are higher in nutritional value and lower in calories, saturated fat, trans fat, sugar, and salt. At a higher rate than proteins or fats, carbohydrates ("carbs") cause the patient's blood sugar levels to increase after consumption. Because carbohydrates often have the biggest impact on blood sugar levels, medical professional recommend carb control as an important tool.

Unfortunately, as many medical professionals have realized, most patients never comply with their recommend diet and frequently, consume too much food by volume and/or weight. Even if the patients are currently receiving some diabetes therapy, the patients often intake excessive amounts of calories, carbohydrates, fats, and/or the like, which negatively affects their health with high blood sugar levels and counteracts the effectiveness of their current diabetes therapy.

Various factors can be used to determine to what extent the patient's blood sugar level is likely to increase or decrease based on a particular food item's portion size and/or other nutrition information. Some devices, systems, and techniques may be programmed with these factors in order to estimate the increase or decrease. Some devices, systems, and techniques improve upon an accuracy in the estimation by accurately measuring the particular food item's volume, for example, from mesh models of the particular food item. By doing so, the devices, systems, and techniques described herein may coordinate the patient's meals and medications such that the patient receives a most effective treatment for diabetes.

In addition to improved effectiveness, the patient may benefit from the devices, systems, and techniques described herein preventing the negative effects of unhealthy blood sugar levels. For instance, by calibrating the patient's therapy around the patient's diet, some devices, systems, and techniques may prevent hypoglycemia and/or hyperglycemia—where too little food or too much food in proportion to the patient's diabetes treatment schedule results in low or high blood sugar, respectively. Although the present disclosure often refers to insulin as the diabetes treatment, the devices, systems, and techniques described herein may apply to the other medications.

Some devices, systems, and techniques described in this disclosure provide the patient and/or the patient's device(s) various data including information identifying a particular food item (e.g., by name or type) as well as the particular food items' portion size or volume information and nutrition information. Some devices, systems, and techniques described in this disclosure provide similar information for a combination of food items. These devices, systems, and techniques provide the patient with the benefit of knowing how food items may affect their blood sugar levels if consumed. If the patient decides to consume the particular food item, disregarding the potential negative effects, some devices, systems, and techniques determine an appropriate diabetes therapy to offset those negative effects (e.g., the increased blood sugar level). In some examples, the patient's current diabetes therapy can be modified with a more effective treatment type, amount, and/or delivery time.

While the patient does not have to eliminate carbs, even if that patient has diabetes, the amount of carbs the patient can have and still maintain a blood sugar level in the target range depends on a number of factors including age, weight, activity level, and other factors. Another factor may be the particular food item's type. As one reason, some carbohydrates, such as fruits, vegetables and whole grains, are better for the patient's glucose management than others. Sugar-sweetened beverages tend to be high in calories, carbohydrates, and offer the patient a trivial nutrition value. In addition, these beverages cause the blood sugar level to rise quickly, possibly requiring an earlier treatment that currently scheduled. Some devices, systems, and techniques may attempt to output content warning the patient to avoid sugar-sweetened beverages if the patient is considering consuming such a beverage or is currently consuming that beverage. On the other hand, if the patient is currently experiencing a low blood sugar level, sugar-sweetened beverages, such as soda, juice and sports drinks may quickly raise the patient's blood sugar back to a healthier level.

Although carbohydrates often have the biggest impact on blood sugar levels, other nutrition information (e.g., calories) for the particular food item may impact the effectiveness of the patient's next insulin dosage. Another factor may be fiber content, which helps keep the blood sugar level stable. Portion size (e.g., extra-large sweetened beverages) may also affect the blood sugar level and similar to carbs, various factors can be used to determine to what extent the blood sugar level is likely to increase or decrease based on the particular food item's portion size. These and other factors described above may be programmed into one or more devices, systems, and techniques that are configured to determine whether the patient's glucose level is likely to increase or decrease if a particular food item is consumed. For at least this reason, the patient may realize a substantial benefit from accurate counting of carbohydrates, in addition to other macronutrients like fiber, in that patient's food items.

Because carbohydrate counting can be an important tool for managing blood sugar levels, some devices, systems, and techniques described herein may be operative to count carbs in foods and beverages that the patient is eating or about to eat and dynamically adapt the patient's next insulin dosage in response to the patient eating an excessive number of carbs or eating insufficient number of carbs. In some examples, devices, systems, and techniques described herein may be configured to avoid delivering more insulin than needed (e.g., if the patient has an insulin surplus due to eating the insufficient number of carbs) or to start delivering more insulin (e.g., if the patient has an insulin deficiency due to eating the excessive number of carbs). Some devices, systems, and techniques may determine a treatment type of the patient's next insulin dosage and whether that type is appropriate for controlling the patient's expected blood sugar level, which may be low (e.g., after eating the insufficient number of carbs) or high (e.g., after eating the excessive number of carbs). In one example, some devices, systems, and techniques may determine that Bolus insulin is not suitable for the patient's expected blood sugar level after detecting little or no carbohydrates in the food item(s) eaten by the patient (if any) and as a correction, modify the next scheduled insulin dosage to a more appropriate treatment type such as Basal insulin; conversely, these devices, systems, and techniques may determine that the Bolus insulin treatment type is appropriate for the patient's expected blood sugar level after detecting excessive carbohydrates in the food item(s) eaten by the patient. In some instances, even if the patient's next insulin dosage is a Bolus insulin dosage, that dosage may still not appropriate because the excessive carbs in the particular food item diminishes the effectives of that insulin dose. Some devices, systems, and techniques may a modify both the insulin type and the amount of the next insulin dosage. In addition or as an alternative, some devices, systems, and techniques may schedule the next insulin dosage to an earlier time (e.g., to increase the insulin in the patient's body) or a later time (e.g., to decrease the insulin in the patient's body).

Therefore, having accurate carbohydrate counts and/or other nutritional facts may enable some devices, systems, and techniques to effectuate modifications to the patient's diabetes treatment schedule, amount, and/or type without affecting the patient's health. To accomplish such modifications, the present disclosure describes devices, systems, and techniques that may be configured to accurately determine a food item's portion size/volume and from that determination, the food item's nutritional content including a precise carbohydrate count. Some devices, systems, and techniques may be configured to utilize that precise carbohydrate count (and/or other nutritional information) to estimate whether the patient's blood sugar level is expected to increase or decrease.

FIG. 1 is a block diagram illustrating an example system for delivering or guiding therapy dosage, in accordance with one or more examples described in this disclosure. FIG. 1 illustrates system 10A that includes patient 12, insulin pump 14, tubing 16, infusion set 18, sensor 20, which may be a glucose sensor, wearable device(s) 22, patient device 24, and cloud 26. Cloud 26 represents a local, wide area or global computing network including one or more processors 28A-28N ("one or more processors 28") and a food library 29. In some examples, food library 29 may be stored on patient device 24 rather than or in addition to cloud 26. Although FIG. 1 depicts the example system as having wearable device 22A on patient 12's wrist and wearable device 22B on patient 12's head, it is possible that other example systems may have fewer, more, and/or different wearable devices 22.

As illustrated in FIG. 1, system 10A includes cloud 26 that includes one or more processors 28. For example, cloud 26 includes a plurality of network devices (e.g., servers), and the plurality of devices each include one or more processors. One or more processors 28 may be processors of the plurality of network devices, and may be located within a single one of the network devices, or may be distributed across two or more of the network devices. Cloud 26 represents a cloud infrastructure that supports one or more processors 28 on which applications or operations requested by one or more users run. For example, cloud 26 provides cloud computing for using one or more processors 28, to store, manage, and process data on the network devices, rather than by patient device 24 or one of wearable devices 22. One or more processors 28 may share data or resources for performing computations, and may be part of computing servers, web servers, database servers, and the like. One or more processors 28 may be in network devices (e.g., servers) within a datacenter or may be distributed across multiple datacenters. In some cases, the datacenters may be in different geographical locations.

One or more processors 28, as well as other processing circuitry described herein, can include any one or more microprocessors, digital signal processors (DSPs), application specific integrated circuits (ASICs), field programmable gate arrays (FPGAs), or any other equivalent integrated or discrete logic circuitry, as well as any combinations of such components. The functions attributed one or more processors 28, as well as other processing circuitry described herein, herein may be embodied as hardware, firmware, software or any combination thereof.

One or more processors 28 may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. One or more processors 28 may include arithmetic logic units (ALUs), elementary function units (EFUs), digital circuits, analog circuits, and/or programmable cores, formed from programmable circuits. In examples where the operations of one or more processors 28 are performed using software executed by the programmable circuits, memory (e.g., on the servers) accessible by one or more processors 28 may store the object code of the software that one or more processors 28 receive and execute.

In some examples, the various components may determine changes to therapy based on determination of glucose level for sensor 20. The present disclosure may describe "therapy" as a reference to patient 12's scheduled diabetes treatments where at certain time(s) the example system delivers an amount of a specific treatment type. Patient 12 may receive this treatment at a fixed time in the day (e.g., noon) or before/during/after an event (e.g., a meal event). As described herein, patient 12's diet may play a significant role in the therapy and depending on which food items are consumed by patient 12, the various components may determine an appropriate treatment type and/or amount to delivery (which may or may not differ from a scheduled treatment type and/or amount).

Patient 12 may be diabetic (e.g., Type 1 diabetic or Type 2 diabetic), and therefore, the glucose level in patient 12 may be uncontrolled without delivery of supplemental insulin. For example, patient 12 may not produce sufficient insulin to control the glucose level or the amount of insulin that patient 12 produces may not be sufficient due to insulin resistance that patient 12 may have developed. The present disclosure may in certain instances describe glucose level as "blood sugar" and vice versa.

To receive the supplemental insulin, patient 12 may carry insulin pump 14 that couples to tubing 16 for delivery of insulin into patient 12. Infusion set 18 may connect to the skin of patient 12 and include a cannula to deliver insulin into patient 12. Sensor 20 may also be coupled to patient 12 to measure glucose level in patient 12. Insulin pump 14, tubing 16, infusion set 18, and sensor 20 may together form an insulin pump system. One example of the insulin pump system is the MINIMED™ 670G INSULIN PUMP SYSTEM by Medtronic, Inc. However, other examples of insulin pump systems may be used and the example techniques should not be considered limited to the MINIMED™ 670G INSULIN PUMP SYSTEM. For example, the techniques described in this disclosure may be utilized in insulin pump systems that include wireless communication capabilities. However, the example techniques should not be considered limited to insulin pump systems with wireless communication capabilities, and other types of communication, such as wired communication, may be possible. In another example, insulin pump 14, tubing 16, infusion set 18, and/or sensor 20 may be contained in the same housing (e.g., in a patch pump).

Insulin pump 14 may be a relatively small device that patient 12 can place in different locations. For instance, patient 12 may clip insulin pump 14 to the waistband of pants worn by patient 12. In some examples, to be discreet, patient 12 may place insulin pump 14 in a pocket. In general, insulin pump 14 can be worn in various places and patient 12 may place insulin pump 14 in a location based on the particular clothes patient 12 is wearing.

To deliver insulin, insulin pump 14 includes one or more reservoirs (e.g., two reservoirs). A reservoir may be a plastic cartridge that holds up to N units of insulin (e.g., up to 300 units of insulin) and is locked into insulin pump 14. Insulin pump 14 may be a battery powered device that is powered by replaceable and/or rechargeable batteries.

Tubing 16, sometimes called a catheter, connects on a first end to a reservoir in insulin pump 14 and connects on a second end to infusion set 18. Tubing 16 may carry the insulin from the reservoir of insulin pump 14 to patient 12. Tubing 16 may be flexible, allowing for looping or bends to minimize concern of tubing 16 becoming detached from insulin pump 14 or infusion set 18 or concern from tubing 16 breaking.

Infusion set 18 may include a thin cannula that patient 12 inserts into a layer of fat under the skin (e.g., subcutaneous connection). Infusion set 18 may rest near the stomach of patient 12. The insulin travels from the reservoir of insulin pump 14, through tubing 16, and through the cannula in infusion set 18, and into patient 12. In some examples, patient 12 may utilize an infusion set insertion device. Patient 12 may place infusion set 18 into the infusion set insertion device, and with a push of a button on the infusion set insertion device, the infusion set insertion device may insert the cannula of infusion set 18 into the layer of fat of patient 12, and infusion set 18 may rest on top of the skin of the patient with the cannula inserted into the layer of fat of patient 12.

Sensor 20 may include a cannula that is inserted under the skin of patient 12, such as near the stomach of patient 12 or in the arm of patient 12 (e.g., subcutaneous connection). Sensor 20 may be configured to measure the interstitial glucose level, which is the glucose found in the fluid between the cells of patient 12. Sensor 20 may be configured to continuously or periodically sample the glucose level and rate of change of the glucose level over time. In some examples, sensor 20 may be referred to as a continuous glucose monitor (CGM).

In one or more examples, insulin pump 14 and sensor 20, and the various components illustrated in FIG. 1, may together form a closed-loop therapy delivery system. For example, patient 12 may set a target glucose level, usually measured in units of milligrams per deciliter, on insulin pump 14. Insulin pump 14 may receive the current glucose level from sensor 20, and in response may increase or decrease the amount of insulin delivered to patient 12. For example, if the current glucose level is higher than the target glucose level, insulin pump 14 may increase the insulin. If the current glucose level is lower than the target glucose level, insulin pump 14 may temporarily cease delivery of the insulin. Insulin pump 14 may be considered as an example of an automated insulin delivery (AID) device. Other examples of AID devices may be possible, and the techniques described in this disclosure may be applicable to other AID devices.

For example, insulin pump 14 and sensor 20 may be configured to operate together to mimic some of the ways in which a healthy pancreas works. Insulin pump 14 may be configured to deliver basal insulin, which is a small amount of insulin released continuously throughout the day. There may be times when glucose levels increase, such as due to eating or some other activity that patient 12 undertakes. Insulin pump 14 may be configured to deliver bolus insulin on demand in association with food intake or to correct an undesirably high glucose level in the bloodstream. In one or more examples, if the glucose level rises above a target level, then insulin pump 14 may increase the bolus insulin to address the increase in glucose level. Insulin pump 14 may be configured to compute basal and bolus insulin delivery, and deliver the basal and bolus insulin accordingly. For instance, insulin pump 14 may determine the amount of basal insulin to deliver continuously, and then determine the amount of bolus insulin to deliver to reduce glucose level in response to an increase in glucose level due to eating or some other event.

Accordingly, in some examples, sensor 20 may sample glucose level and rate of change in glucose level over time. Sensor 20 may output the glucose level to insulin pump 14 (e.g., through a wireless link connection like Bluetooth or BLE). Insulin pump 14 may compare the glucose level to a target glucose level (e.g., as set by patient 12 or clinician), and adjust the insulin dosage based on the comparison. In some examples, sensor 20 may also output a predicted glucose level (e.g., where glucose level is expected to be in the next 30 minutes), and insulin pump 14 may adjust insulin delivery based on the predicted glucose level.

As described above, patient 12 or a clinician may set the target glucose level on insulin pump 14. There may be various ways in which patient 12 or the clinician may set the target glucose level on insulin pump 14. As one example, patient 12 or the clinician may utilize patient device 24 to communicate with insulin pump 14. Examples of patient device 24 include mobile devices, such as smartphones or tablet computers, laptop computers, and the like. In some examples, patient device 24 may be a special programmer or controller for insulin pump 14. Although FIG. 1 illustrates one patient device 24, in some examples, there may be a plurality of patient devices. For instance, system 10A may include a mobile device and a controller, each of which are examples of patient device 24. For ease of description only, the example techniques are described with respect to patient device 24, with the understanding that patient device 24 may be one or more patient devices.

Patient device 24 may also be configured to interface with sensor 20. As one example, patient device 24 may receive information from sensor 20 through insulin pump 14, where insulin pump 14 relays the information between patient device 24 and sensor 20. As another example, patient device 24 may receive information (e.g., glucose level or rate of change of glucose level) directly from sensor 20 (e.g., through a wireless link).

In one or more examples, patient device 24 may display a user interface with which patient 12 or the clinician may control insulin pump 14. For example, patient device 24 may display a screen that allows patient 12 or the clinician to enter the target glucose level. As another example, patient device 24 may display a screen that outputs the current and/or past glucose level. In some examples, patient device 24 may output notifications to patient 12, such as notifications if the glucose level is too high or too low, as well as notifications regarding any action that patient 12 needs to take. For example, some notifications may include warnings for patient 12 to avoid a particular food item because consuming that food item is likely to raise patient 12's glucose level to an unhealthy level. As another example, if the batteries of insulin pump 14 are low on charge, then insulin pump 14 may output a low battery indication to patient device 24, and patient device 24 may in turn output a notification to patient 12 to replace or recharge the batteries.

Controlling insulin pump 14 through patient device 24 is one example, and should not be considered limiting. For example, insulin pump 14 may include a user interface (e.g., pushbuttons) that allow patient 12 or the clinician to set the various glucose levels of insulin pump 14. Also, in some examples, insulin pump 14 itself, or in addition to patient device 24, may be configured to output notifications to patient 12. For instance, if the glucose level is too high or too low, insulin pump 14 may output an audible or haptic output. As another example, if the battery is low, then insulin pump 14 may output a low battery indication on a display of insulin pump 14.

The above describes examples ways in which insulin pump 14 may deliver insulin to patient 12 based on the current glucose levels (e.g., as measured by sensor 20). In some cases, there may be therapeutic gains by proactively delivering insulin to patient 12, rather than reacting to when glucose levels become too high or too low. Based on information identifying which food item(s) patient 12 plans to consume, one or more processors 28 may accurately predict an increase or decrease in patient 12's glucose level. One or more processors 28 may analyze such information to determine how much patient 12's glucose level will likely change by consuming the food item(s).

As described herein, patient device 24 and/or cloud 26 may support the above-mentioned determination by maintaining (e.g., in food library 29) food item information for each food item of a plurality of food items for potential consumption. In some examples, food library 29 may be configured to store, for each food item, nutrition information, volume information, and any other food item information to be used in determining how much patient 12's glucose level will likely increase or decrease by consuming that food item. To illustrate by way of example, food library 29 may store food item information for a single apple including a mapping between a volume measurement and an expected carbohydrate count in an apple having a similar volume measurement. One or more processors 28 and/or processing circuitry 32 may determine the volume measurement from a mesh model of the single apple, access food library 29 to lookup the above example mapping, and then, use the expected carbohydrate count to determine the likely increase or decrease to patient 12's glucose level. In some examples, food library 29 may specify one or more factors and other indicia of either an increase or a decrease in patient 12's glucose level. Examples of such factors include thresholds, conditions, and other criterion for the food item information to satisfy. For a single apple, food library 29 may define one or more thresholds/conditions on counts of calories, carbohydrates, grams of fat, and/or other nutritional facts that, if satisfied, indicate an increase or decrease in the glucose level. For example, if the apple's nutritional content (e.g., carbohydrate count) exceeds respective threshold counts (e.g., daily recommended amounts), consuming that apple is likely to increase patient 12's glucose level. In other examples, food library 29 may define one or more thresholds/conditions on a portion size or a total volume of the food item that, if satisfied, is likely to increase or decrease the glucose level. For example, by providing patient 12 with excessive amounts of calories, carbohydrates, grams of fat, and/or the like, consuming that apple is likely to increase patient 12's glucose level.

In addition to patient 12's diet, the glucose level in patient 12 may increase or decrease due to other particular user actions. As one example, the glucose level in patient 12 may increase due to patient 12 engaging in an activity like eating or exercising. In some examples, there may be therapeutic gains if it is possible to determine that patient 12 is engaging in the activity or intends to engage in the activity, and delivering insulin based on the determination that patient 12 is engaging in the activity or intends on engaging in the activity.

As described herein, therapy information for patient 12 may include a treatment schedule for insulin pump 14 and/or sensor 20 to execute and examples of such a schedule may indicate planned treatment deliveries of specific amounts of an insulin type. Based on patient 12's diet, one or more processors 28 may adjust the treatment schedule by modifying a type or an amount of a planned treatment. For example, if patient 12 decides to eat one or more food items with excessive amounts of calories, carbohydrates, grams of fat, and/or the like, causing an unhealthy increase in patient 12's glucose level, one or more processors 28 may modify the therapy information to account for patient 12's food consumption. In some examples, by increasing an amount of insulin, changing a type of insulin, and/or adjusting a time at which insulin is to be delivered in accordance with next planned injection, one or more processors 28 may return patient 12 back to a healthy glucose level. Similarly, if patient 12 decides not to eat (e.g., fast) or restrict his/her diet to food items that are low in calories, carbohydrates, grams of fat, and/or the like, resulting in an unhealthy decrease in patient 12's glucose level, one or more processors 28 may modify the therapy information to account for patient 12's food consumption. In some examples, by reducing an amount of insulin, changing a type of insulin, and/or adjusting a time at which insulin is to be delivered in accordance with next planned injection, one or more processors 28 may return patient 12 back to a healthy glucose level.

For example, patient 12 may forget to cause insulin pump 14 to deliver insulin after eating, resulting an insulin shortfall. Alternatively, patient 12 may cause insulin pump 14 to deliver insulin after eating, but patient 12 may have forgotten previously causing insulin pump 14 to deliver insulin for the same meal event, resulting in an excessive insulin dosage. Also, in examples where sensor 20 is utilized, insulin pump 14 may not take any action until after the glucose level is greater than a target level. By proactively determining that patient 12 is engaging in an activity, insulin pump 14 may be able to deliver insulin in such a manner that the glucose level does not rise above the target level or rises only slightly above the target level (i.e., rises by less than what the glucose level would have risen if insulin were not delivered proactively). In some cases, by proactively determining that patient 12 is engaging in an activity and delivering insulin accordingly, the glucose level of patient 12 may increase more slowly.

Although the above describes proactive determination of patient 12 eating and delivering insulin accordingly, the example techniques are not so limited. The example techniques may be utilized for proactively determining an activity that patient 12 is undertaking (e.g., eating, exercising, sleeping, driving, etc.). Insulin pump 14 may then deliver insulin based on the determination of the type of activity patient 12 is undertaking.

As illustrated in FIG. 1, patient 12 may wear wearable devices 22A-22B to avail his/herself of various functionality, including generating at least a portion of the data corresponding to a representation of an object suspected to be a food item and/or generating data indicating consumption of the object by the patient. Examples of wearable device 22A include a smartwatch or a fitness tracker, either of which may, in some examples, be configured to be worn on a patient's wrist or arm. Another example of wearable device 22A may include an Augmented Reality (AR) bracelet. In one or more examples, wearable device 22A includes inertial measurement unit, such as a six-axis inertial measurement unit. The six-axis inertial measurement unit may couple a 3-axis accelerometer with a 3-axis gyroscope. Accelerometers measure linear acceleration, while gyroscopes measure rotational motion. Wearable device 22A may be configured to determine one or more movement characteristics of patient 12. Examples of the one or more movement characteristics include values relating to frequency, amplitude, trajectory, position, velocity, acceleration and/or pattern of movement instantaneously or over time. The frequency of movement of the patient's arm may refer to how many times patient 12 repeated a movement within a certain time (e.g., such as frequency of movement back and forth between two positions).

However, the example techniques are not so limited. Patient 12 may wear wearable devices 22 on a finger, forearm, bicep, head, and/or face. In one example, patient 12 may wear wearable device(s) 22 anywhere that can be used to determine gestures indicative of eating, such as movement characteristics of the arm. In one example, patient 12 may wear wearable devices 22A or 22B anywhere that can be used to capture 2D/3D representations of objects that are within patient 12's proximity. Devices that combines computing components (e.g., memory and a processor) with eyeglasses (e.g., smart glasses) are examples of wearable device 22B to capture 2D/3D representations. In some examples, wearable devices 22A or 22B may be configured to determine, based on the detected gestures (e.g., movement and/or posture characteristics of the arm of patient 12) and/or 2D/3D object representations (e.g., mesh models), the particular activity patient 12 is undertaking. For example, wearable devices 22A or 22B may be configured to determine whether patient 12 is eating, exercising, driving, sleeping, etc. As another example, wearable devices 22A or 22B may be configured to determine which food item(s) are in the captured object representations. In one example, wearable devices 22A or 22B, in combination with patient device 24 and/or cloud 26, may be configured to determine whether patient 12 is eating a particular food item and if so, whether that food item's nutritional content and/or portion size affects the patient's diabetes therapy. In some examples, patient device 24 may be configured to capture 2D and/or 3D representations of objects that are within patient 12's proximity.

In some examples, wearable devices 22A or 22B may output information indicative of the object representations, the movement and/or posture characteristics of the arm of patient 12, and/or the posture of patient 12 to patient device 24 and/or cloud 26, and patient device 24 and/or cloud 26 may be configured to determine the activity patient 12 is undertaking. A particular food item being consumed by patient 12 may define a mesh model that represents the particular food item as a volumetric collection of polygons. Patient device 24 and/or cloud 26 may compute a volume measurement from the mesh model and then, use that volume measurement to estimate the particular food item's nutritional content and/or portion size (e.g., serving size). To determine how much patient 12's glucose level will likely change by consuming the particular food item given the estimated nutritional content and/or portion size, patient device 24 and/or cloud 26 may employ a mathematical function or probability model that is configured to accept, as input variables, factors corresponding to the estimated nutritional content and/or portion size and generate, as output data, an expected amount of increase or decrease in the glucose level of patient 12. In some examples, the mathematical function or probability model may be static and pre-determined by health professionals. In other examples, patient device 24 and/or cloud 26 may employ machine learning techniques to dynamically adjust the mathematical function or probability model in response to feedback (e.g., "learning") in a manner that improves upon an accuracy of the mathematical function or probability model.

The manner in which patient 12 is moving his or her arm (i.e., the movement characteristics) may refer to the direction, angle, and orientation of the movement of the arm of patient 12, including values relating to frequency, amplitude, trajectory, position, velocity, acceleration and/or pattern of movement instantaneously or over time. As an example, if patient 12 is eating, then the arm of patient 12 will be oriented in a particular way (e.g., thumb is facing towards the body of patient 12), the angle of movement of the arm will be approximately a 90-degree movement (e.g., starting from plate to mouth), and the direction of movement of the arm will be a path that follows from plate to mouth. The forward/backward, up/down, pitch, roll, yaw measurements from wearable device 22A may be indicative of the manner in which patient 12 is moving his or her arm. Also, patient 12 may have a certain frequency at which patient 12 moves his or her arm or a pattern at which patient 12 moves his or her arm that is more indicative of eating, as compared to other activities, like smoking or vaping, where patient 12 may raise his or her arm to his or her mouth.

In addition or as an alternative, patient 12 may operate one or more sensors in wearable devices 22A or 22B as part of a process to determine the activity patient 12 is undertaking and/or whether that activity interferes with patient 12's diabetes therapy, an example of which includes determining which particular food item(s) patient 12 is eating or considering eating and/or determine whether the particular food item(s) is likely to increase or decrease patient 12's glucose level (e.g., to an unhealthy level). Patient 12 may avail his/herself of imaging sensing equipment in wearable devices 22A or 22B to create a three-dimensional map of an immediate environment (e.g., from his/her perspective) that includes data (e.g., point clouds) representing one or more objects suspected to be food items within that immediate environment.

The present disclosure does not limit the example system of FIG. 1 to any one or more imaging sensors, and thus, wearable devices 22A or 22B and/or patient device 24 may include any imaging sensor capable of generating the three-dimensional (3D) map as a representation of at least one food item. In some examples, imaging sensors may use light (e.g., from infrared (IR) lasers) and a time-of-flight (TOF) technique to measure a distance to an object suspected to be a food item in an environment. Examples of wearable devices 22 and/or patient device 24, implementing 3D depth sensing technologies such as Light Detection and Ranging (LIDAR), may create point cloud data for the 3D map by having a LiDAR sensor emit an invisible laser light and then, estimate the distance to objects/suspected food items based on measuring a trip time for the light that is reflected from the object to return to the LiDAR sensor. As an alternative, examples of wearable device 22 and/or patient device 24 may employ Vertical-cavity surface-emitting lasers (VCSEL) sensors, scannerless LiDAR sensors, and/or 3D ToF sensors to create 3D point cloud data for the 3D map.

Depth frameworks may enhance the 3D map, for example, by improving upon the map's resolution and/or increasing the object's precision in its representation of a food item. Some frameworks combine depth points measured by a LIDAR Sensor (e.g., a LiDAR Scanner), image data captured by a 2D camera unit or sensor, and patient activity data determined by an inertial measurement unit and create, from the map, a more detailed and complete understanding of the immediate environment (e.g., as a scene). Some technologies may transform the map into rich content (e.g., multimedia content).

3D depth sensors including LiDAR sensors may be installed in smartglasses, smartwatches, AR/VR googles, and other examples of wearable device 22B. 3D depth sensors including LiDAR sensors may be installed in handheld tablet computers, smartphones, and other examples of patient device 24. In some examples where one or more LiDAR sensors are integrated into patient device 24 and/or wearable device 22B, patient 12 may utilize only patient device 24 to capture 2D, 3D, or both 2D and 3D representations of food items (e.g., instead of wearable devices 22A or 22B). In some examples where patient 12 utilizes a combination of wearable devices 22A and/or 22B and patient device 24, patient 12 may use either one of or both LiDAR sensor embodiments to generate the three-dimensional map to include point cloud data representing the object in that environment. Patient 12 may utilize computing devices (e.g., patient device 24) with an integrated LiDAR sensor because that sensor contributes a trivial amount to any device's cost. Instead of radio waves or visible light waves, the LIDAR sensor's source is infrared light waves, allowing the LiDAR sensor to capture LiDAR images regardless of ambient light. Although traditional 2D cameras may provide better image resolution, LIDAR sensors operate in day or night conditions and 3D LIDAR sensors, in particular, provide superior range accuracy image information.

Wearable devices 22A or 22B may be programmed to operate autonomously and/or with minimal input or control by patient 12, for example, by monitoring patient 12's gestures to detect when patient 12 is eating (e.g., a meal event), automatically capturing LiDAR representations (e.g., maps) of any food item being consumed or about to be consumed upon a positive detection, and then, determining whether any of the consumed or to be consumed food items is likely to increase or decrease patient 12's glucose level (e.g., to an unhealthy level).

In some examples, wearable devices 22A or 22B, possibly in combination with patient device 24 and/or cloud 26, may estimate an amount of a treatment (e.g., insulin) that is needed to counteract the glucose level increase or decrease due to patient 12's consumption of certain quantities describing one or more food items (e.g., a solid food, a liquid drink, or a mixture of suspended edible foods in a drinkable liquid (e.g., soup)). Wearable devices 22A or 22B, possibly in combination with patient device 24 and/or cloud 26, may generate an accurate estimate of some quantity (e.g., a carbohydrate count, a number of servings, and/or the like) in any given food item's content, for example, based on accurate measurements of that food item's mass and/or volume (e.g., portion size).

In some examples, components of wearable devices 22A or 22B and/or patient device 24 may be integrated with one or more imaging sensors, such as a camera unit configured to capture a two-dimensional image of the immediate environment including an object suspected to be a food item. Examples of patient device 24 may include a smart tablet, a laptop or desktop computer, any stand-alone 2D camera system, and/or the like. Example combinations of wearable devices 22A or 22B and patient device 24 may include an Augmented Reality (AR) headset with an internal computing resources or smart glasses. Some examples of wearable devices 22A or 22B and/or patient device 24 include devices with a 3D LiDAR sensor and a 2D camera unit or sensor, for example, to enable simultaneous, concurrent, or sequential capture of representations of objects suspected to be food items.

Patient 12 may wear wearable device 22B on his or her head (e.g., face). Examples of such a wearable device 22B includes a smart glasses, goggles as part of a headset (e.g., an Augmented Reality/Virtual Reality (AR/VR) headset), goggles without a headset, a necklace (e.g., an AR necklace), and any other gear configured to be worn on patient 12's head, neck, or face. Any one of these examples allow patient 12 to visualize a food item and capture at least one representation of that food item. Some example representations may depict the food item as an object having color data, geometry data, position data, size data, and/or other data. Patient 12 may wear on his/her head wearable device 22B while performing normal, routine activities (e.g., food consumption) such that when patient 12 is eating or preparing to eat imminently, wearable device 22B may capture data-rich representations of any food item and submit to cloud 26 a query regarding each food item's potential impact on patient 12's health (e.g., to patient 12's glucose level).

Wearable device 22B and/or patient device 24 may be provided with information (e.g., via user input or a communication channel) that wearable device 22B and/or patient device 24 utilize to determine the particular activity patient 12 is undertaking. Eating one or more particular food items (i.e., food consumption) may be an example of that particular activity and as described herein, wearable device 22B and/or patient device 24 may utilize downloaded information (e.g., food item information and/or therapy information) from cloud 26 (e.g., from food library 29) to determine whether eating the one or more particular food items is likely to increase or decrease patient 12's glucose level (e.g., to an unhealthy level) and whether that increase or decrease is likely to interfere with patient 12's diabetes therapy. In some examples, patient 12 may provide wearable device 22B and/or patient device 24 with various input including information identifying the one or more particular food items. In other examples, one or more processors 28 of cloud 26 may perform the identification of each particular food item (e.g., using food library 29) and provide wearable device 22B and/or patient device 24 with the information identifying the one or more particular food items.

Accordingly, in one or more examples, wearable device 22B and/or patient device 24 may "learn" to determine whether patient 12 is undertaking a particular activity, such as eating or intending on eating a particular food item. However, the computing resources of wearable device 22B and patient device 24 may be insufficient to performing the learning needed to determine whether patient 12 is undertaking a particular activity. It may be possible for the computing resources of wearable device 22 and patient device 24 to be sufficient to perform the learning, but for ease of description only, the following is described with respect to one or more processors 28 in cloud 26.

In some examples, one or more processors 28 may be configured to determine patterns from gesture movements (e.g., as one or more movement characteristics determined by wearable devices 22A or 22B), and configured to determine a particular activity patient 12 is undertaking. One or more processors 28 may provide responsive real-time cloud services that can, on a responsive real-time basis, determine the activity patient 12 is undertaking, and in some examples, provide recommended therapy (e.g., insulin dosage amount). Cloud 26 and patient device 24 may communicate via Wi-Fi or through a carrier network.

For example, as described above, in some examples, wearable device 22B and/or patient device 24 may be configured to determine that patient 12 is undertaking an activity. However, in some examples, patient device 24 may output information indicative of the movement characteristics of movement of the arm of patient 12 to cloud 26, and possibly with other contextual information like location or time of day. One or more processors 28 of cloud 26 may then determine the activity patient 12 is undertaking. Insulin pump 14 may then deliver insulin based on the determined activity of patient 12.

There may be various factors that can be used separately or in combination with patient input to determine whether patient 12 is engaging in an activity, such as eating or planning to eat a particular food item. As one example, patient 12 may engage in the activity at regular time intervals. As another example, patient 12 may engage in the activity at certain locations. Time of day and location are two examples of contextual information that can be used to determine whether patient 12 is engaging in the activity. However, there may be other examples of contextual information for patient 12 such as sleep pattern, body temperature, stress level (e.g., based on pulse and respiration), heart rate, etc. In general, there may be various biometric sensors (e.g., to measure temperature, pulse/heart rate, breathing rate, etc.), which may be part of wearable devices 22A or 22B or may be separate sensors. In some examples, the biometric sensors may be part of sensor 20.

Other examples of contextual information for patient 12 include possible food items (e.g., solid meat or vegetables and liquids beverages) for consumption. Eating (e.g., during meal events) is an activity engaged in by patient 12 and identifying which food items are being consumed while eating may serve an important role in diabetes insulin delivery for that patient 12. In various aspects including nutrition and volume, two food items may differ by small or large margins. When a chicken drumstick is compared to an apple, for instance, each provides different nutrients and contributes a different amount to patient 12's body mass. Techniques described herein may be directed towards identifying a particular food item from various information including the contextual information described herein and as part of identifying the food item, some techniques may be configured to determine supporting information (e.g., therapy information for the patient and other food item information such as nutrient and volume information) for the diabetes insulin delivery for patient 12.

The contextual information for patient 12 may include conditional information. For example, patient 12 may eat every 3 hours, but the exact times of when patient 12 eats may be different. In another example, patient 12 may eat a meal every time he is at particular location (e.g., a restaurant, food court, cafeteria). In some examples, the conditional information may be a determination of whether patient 12 has eaten and if a certain amount of time (e.g., 3 hours) has passed since patient 12 ate. In general, any information that establishes a pattern of behavior may be utilized to determine whether patient 12 is engaging in a particular activity (e.g., eating a particular food item such as a steak, an apple, or a tomato).

Wearable devices 22A or 22B and/or patient device 24 may be configured to identify which food items patient 12 is eating or considering eating and provide each identification to one or more processors 28 of cloud 26. In other examples, wearable devices 22A or 22B and/or patient device 24 may communicate to cloud 26 data corresponding to a representation of an object suspected to be a food item, and possibly with other contextual information like location or time of day. In turn, one or more processors 28 of cloud 26 may identify which food items patient 12 is eating or considering eating and generate food item information (e.g., nutrition and/or volume information) in support of the diabetes insulin delivery for patient 12.

In some examples, wearable devices 22A or 22B and/or patient device 24 may be configured with access to food library 29 or at least a portion thereof. As an example, wearable devices 22A or 22B and/or patient device 24 may store information identifying different food items of which examples include image data, point cloud data, and other representations (e.g., two-dimensional and three-dimensional representations). One example representation, image data, may be a (two-dimensional) pixelized and/or a (three-dimensional) voxelized address space of color intensities for the object (with or without a background environment). Another example representation, point cloud data, includes groups of three-dimensional points of a reflecting surface geometry located in space based on data determined by a sensor (e.g., a LiDAR sensor) emitting pulses of energy in a direction of the reflecting surface geometry and measuring return trips.

Based on any representation of an object that patient 12 purports to be a food item and other contextual information, one or more processors 28 of cloud 26 may use food library 29 (e.g., a machine learning model) to determine the nutrient and/or volume information for the purported food item. Food library 29 may be built (e.g., trained) on feature data identifying a number of data points (e.g., features) in any object's representation such that each specific food item may be identified based on presence of specific feature data. For example, amongst other fruits, food library 29 may distinguish an apple by defining apple food items using specific data points as features; hence, if one or more processors 28 of cloud 26 identify of all of these data points in an object's representation, that identification favorably indicates that the object is most likely an apple.

In some examples, wearable devices 22A or 22B and/or patient device 24 may be commercialized user devices, either operating together (as a system) or separately, including those known as smart devices, such as smart mobile phones, tablets, watches, glasses/googles, and/or other mobile computing devices. In some examples, wearable devices 22A or 22B and/or patient device 24 may cooperate with respect to sharing data and/or logic for facilitating determination of nutrients and/or a volume of the purported food item. In some instances, wearable devices 22A or 22B may be a pair of glasses equipped with one or more LiDAR sensors to capture data including one or more representations of an object that is suspected to be a food item and in turn, patient device 24, having access to these one or more object representations, may determine the food item's carbohydrate count (e.g., based on the food type and portion size or volume). If the food item is unknown or not identified by patient 12, patient device 24 (possibly in conjunction with one or more processors 28 of cloud 26) may determine information identifying the food item, for example, as a particular vegetable, fruit, portion of meat or fish, a beverage, a mixture (e.g., soup), and/or the like.

One or more processors 28 may utilize artificial intelligence, such as machine-learning or other data analytics techniques, based on the information determined by and/or collected by wearable devices 22A or 22B and patient device 24 to determine whether patient 12 is engaging in the activity, such as eating or planning to eat a particular food item. As one example, during the initial learning phase, one or more processors 28 may utilize neural network techniques. For example, one or more processors 28 may receive training data from patient 12 that is used to train a classifier executing on one or more processors 28. As described above, one or more processors 28 may receive the training data based on patient confirmation when patient device 24 and/or wearable devices 22A or 22B determine, based on a representation of an object, that patient 12 is engaging in the activity (e.g., the representation matches stored data in food library 29). One or more processors 28 may generate and store a labeled data record that includes the features related to the movement, along with other contextual features, such as time of day or location. One or more processors 28 may train the classifier on a labeled dataset that includes multiple labeled data records, and one or more processors 28 may use the trained classifier to more accurately detect the start of a food intake event.

Other examples that may be used for neural networks include behavior patterns. For example, patient 12 may only eat a particular food after exercising, and always eats that particular food after exercising. Patient 12 may eat at a particular time and/or place. Although described with respect to eating, there may be various conditions that together indicate a pattern in behavior of patient 12 for different activities.

As another example, one or more processors 28 may utilize k-means clustering techniques to determine whether patient 12 is engaging in an activity such as eating a particular food item and, in some examples, whether a portion size and/or a nutritional content or the particular food item is likely to increase or decrease patient 12's glucose level. For example, during the initial learning phase one or more processors 28 may receive different types of contextual information and form clusters, where each cluster represents a behavior of patient 12 (e.g., eating, sleeping, walking, exercising, etc.). For example, patient 12 may enter information (e.g., into patient device 24) indicating that he or she is walking. One or more processors 28 may utilize all the contextual information received when patient 12 is walking to form a first cluster associated with walking. Patient 12 may enter information (e.g., into patient device 24) indicating that he or she is eating and which food item(s) he or she is eating. One or more processors 28 may utilize all the contextual information received when patient 12 is eating to form a second cluster associated with eating, and so on. Then, based on received contextual information, one or more processors 28 may determine which cluster aligns with the contextual information, and determine the activity patient 12 is undertaking. As described in more detail, the type of activity, and a prediction of when the activity will occur, may be utilized to determine when to delivery insulin therapy. There may be other examples of machine learning, and the example techniques are limited to any particular machine learning technique.

There may be various other ways in which one or more processors 28 may determine the activity patient 12 is undertaking. This disclosure provides some example techniques for determining the activity patient 12 is undertaking, but the example techniques should not be considered limiting.

During the initial learning phase, patient 12 may also enter information about the activity that patient 12 is undertaking. For example, with eating, patient 12 may enter information indicating what patient 12 is eating and/or how many carbohydrates there are in the food that patient 12 is eating. As one example, at 9:00 every morning, patient 12 may enter that he or she is having a bagel or enter that the patient 12 is consuming 48 grams of carbohydrates.

In some examples, one or more processors 28 may be configured to determine an amount of insulin (e.g., therapy dosage of bolus insulin) to deliver to patient 12. As one example, memory accessible by one or more processors 28 may store patient parameters of patient 12 (e.g., weight, height, etc.). The memory may also store a look-up table that indicates an amount of bolus insulin that is to be delivered for different patient parameters and different types of foods. One or more processors 28 may access the memory and based on the type of food patient 12 is eating and patient parameters may determine the amount of bolus insulin that patient 12 is to receive.

As another example, one or more processors 28 may be configured to utilize a "digital twin" of patient 12 to determine an amount of bolus insulin patient 12 is to receive. A digital twin may be a digital replica or model of patient 12. The digital twin may be software executing on one or more processors 28. The digital twin may receive, as input, information about what patient 12 ate. Because the digital twin is a digital replica of patient 12, the output from the digital twin may be information about what the glucose level of patient 12 may be after eating, as well as a recommendation of how much bolus insulin to deliver to patient 12 to control the increase the glucose level.

For example, the digital twin may indicate what the correct dose should have been for a meal that patient 12 ate in the past. In one or more examples, patient 12 may enter information indicative of food patient 12 ate and one or more processors 28 may receive information about glucose levels. Utilizing information indicative of food that patient 12 ate and glucose levels, one or more processors 28 may utilize the digital twin to determine what the insulin dose should have been (e.g., based on how the digital twin models how the food will affect the patient's glucose level). Then, at a subsequent time when patient 12 is predicted to eat the same meal, one or more processors 28 may determine what the insulin dose should be based on insulin dose amount that the digital twin had previously determined.

Accordingly, in one or more examples, one or more processors 28 may utilize information about the movement characteristics of movement of arm, eating pace, quantity of food consumption, food content, etc., while also tracking other contextual information. Examples of the contextual information include location information, time of day, wake up time, amount of time since last eaten, calendar event, information about person patient 12 may be meeting, etc. One or more processors 28 may identify patterns and correlations between all these various factors to determine an activity patient 12 undertaking, like eating, walking, sleeping, driving, exercising, etc.

After the initial learning phase, one or more processors 28 may automatically, and with minimal input from patient 12, determine that patient 12 is undertaking a particular activity, and determine an amount of bolus insulin to deliver based on the determination. One or more processors 28 may output the recommendation of the amount of bolus insulin to deliver to patient device 24. Patient device 24, may then in turn, control insulin pump 14 to deliver the determined amount of insulin. As one example, patient device 24 may output to insulin pump 14 the amount of bolus insulin to deliver with or without user confirmation. As another example, patient device 24 may output a target glucose level, and insulin pump 14 may deliver the insulin to achieve the target glucose level. In some examples, it may be possible for one or more processors 28 to output to patient device 24 information indicative of the target glucose level, and patient device 24 may output that information to insulin pump 14. All of these examples may be considered as examples of one or more processors 28 determining an amount of insulin to deliver to patient 12.

The above describes example ways in which to determine if patient 12 is undertaking an activity, determining an amount of insulin to deliver, and causing the amount of insulin to be delivered. The example techniques may require little to no intervention from patient 12. In this manner, there is an increase in likelihood that patient 12 will receive the correct amount of dosage of insulin at the right time, and decrease in likelihood of human error causing issues (e.g., patient 12 forgetting to log meals, forgetting to take insulin, or taking insulin but forgetting to have taken insulin).

While the above example techniques may be beneficial in patient 12 receiving insulin at the right time, this disclosure describes example techniques to further proactively control delivery of insulin to patient 12. Some example techniques proactively monitor patient 12's food consumption for any food item that, if consumed, is likely to disrupt patient 12's glucose level where that disruption is likely to negatively affect (e.g., diminish) the effectiveness of the patient 12's diabetes therapy. These example techniques may be beneficial in patient 12 receiving an effective or "correct" dosage of insulin. Even if patient 12 has a treatment schedule for his/her diabetes therapy, patient 12 may eat a food item that increases patient 12's glucose level beyond a point where a next scheduled dosage can reduce back to a healthy level, rendering ineffective the next scheduled dosage. Some example techniques dynamically change one or more parameters of the current treatment schedule, for example, to modify a treatment type, amount, or time in order to be effective against the increased glucose level.

In order to prepare an effective dosage for patient 12's next injection, some example techniques may rely upon accurate identifications of food items patient 12 is eating or considering eating. If the food item can be identified with a sufficient confidence level, accurate food item information (e.g., nutrition information) may be determined, enabling the example techniques to effectively guide patient 12's therapy. To accomplish at least a sufficient level of accuracy, some example techniques may leverage food library 29 in a mechanism operative to identify each food item (e.g., by name or type), for example, by analyzing representations of objects suspected to be any one of the food items that patient 12 is eating or considering eating. One example of food library 29 may be a database of food item information records where each record stores various data attributes describing a particular food item, such as a food item identifier, a food item name and/or type, a computer representation of that particular food item, nutrition information, volume information, and/or the like. Some example techniques designate the food item identifier to operate as the database's index and use the representation of the particular food item (e.g., an apple) to identify other representations of the same particular food item (e.g., another apple).

To illustrate by way of example, patient 12 (e.g., while operating patient device 24 and/or wearable devices 22A or 22B) may capture a representation of an object that patient 12 purports to be the particular food item and submit to cloud 26 that representation for confirmation. One or more processors 28 may analyze the submitted representation for various indicia of the particular food item and if sufficient indicia are present, one or more processors 28 may designate the particular food item as the object's identification and, in some examples, determine a volume (e.g., a portion size) of the particular food item. This disclosure provides below further details regarding the analysis by one or more processors 28; for sake of brevity, one or more processors 28 may compare the submitted representation to stored data (e.g., a stored representation of the particular food item) and if the representations substantially match, one or more processors 28 may designate the particular food item as the object's identification. In some examples, patient 12 may provide the object's representation without any indication of the object's identity (i.e., unknown), resulting in one or more processors 28 comparing the object's representation to representations depicting a plurality of possible food items in an attempt to find the matching particular food item.

After identifying the object as the particular food item and based on stored nutrition information (e.g., carbohydrate count) for the particular food item in food library 29 and/or a volume (e.g., a portion size) of the particular food item, one or more processors 28 may determine to what extent consuming the object is likely to impact patient 12's glucose level. Assuming patient 12 consumes the object, one or more processors 28 may prepare for changes in patient 12's glucose level by determining an appropriate treatment type, amount, and/or delivery time and, in some instances, modifying patient 12's current diabetes therapy schedule and other information (e.g., determine a pre-meal and/or post-meal bolus amount). One or more processors 28 may instruct patient device 24 to output content notifying patient 12 of the glucose level changes and in turn, patient device 24 may output the content before, during, or after patient 12's consumption of the particular food item. Patient device 24 may output such content as directed by cloud 26 or autonomously. In examples where patient device 24 outputs a warning with sufficient time to prevent patient 12's consumption, patient device 24 may utilize one or more sensors to determine whether patient 12 actually consumed the particular food item or heeded the warning instead. For example, patient device 24 may use patient activity data from sensors such as inertial measurement units and accelerometers, determine whether patient 12's arm movements indicate gestures for eating. In addition or as an alternative to inertial measurement units, patient device 24 may access sensor data from a bioimpedance sensor, a temperature sensor, an electrode sensor, an imaging sensor, and/or any other sensor capable of detecting food consumption by patient 12.

It should be noted that while the present disclosure describes one or more processors 28 for determining whether the particular food item is likely to impact patient 12's glucose level, other examples envisioned by the present disclosure may instead employ patient device 24 and processing circuitry 32 for determining whether and how the particular food item is likely to impact patient 12's glucose level. In such examples, processing circuitry 32 may maintain food library 29 in patient device 24. Other examples may coordinate execution of the example techniques between patient device 24 and cloud 26, for instance, by having one or more processors 28 maintain food library 29 to provide a copy thereof to processing circuitry 32.

Although the above examples describe advantageously using various sensors for confirming patient 12's food consumption, the present disclosure describes additional ways to advance the proactive monitoring of patient 12's food consumption with the benefit of sensor data from the various sensors described herein. Imaging sensors encompass one example type or group of sensors and, in general, measure color information such as color intensities, light information such as luminous intensity, and/or the like.

In the example system depicted in FIG. 1, one or more imaging sensors may be part of wearable devices 22A or 22B, patient device 24, sensor 20, or may be separate sensors. Wearable devices 22A or 22B, patient device 24, and/or cloud 26 may instrument one or more imaging sensors to operate on behalf of patient 12 and to benefit patient 12's therapy, for example, by capturing, for possible identification using food library 29, representations of objects that patient 12 is eating or about to eat. Examples of the imaging sensors include image or video cameras, LiDAR sensors, sonar sensors, optical sensors, and/or the like. An example image or video camera envisioned by the present disclosure may generate image data of pixelized color information, for example, as color intensity value in a color model such as RGB. An example LiDAR sensor envisioned by the present disclosure may generate point cloud data as a representation of an object suspected to be a food item. In some examples, one or more imaging sensors may be components of a commercialized user device such as one of the above-mentioned smart devices for wearable device(s) 22 and/or patient device 24.

As described in the above example techniques, one or more components of the example system of FIG. 1 (e.g., patient device 24 and/or cloud 26) builds food library 29 to effectuate proactive calibration of patient 12's diabetes therapy based on various food items that are about to be consumed or are being consumed. Patient 12 (via wearable devices 22A or 22B and/or patient device 24) may capture representations of objects (e.g., purporting to be the particular food item or any food item) and benefit from an automatic titration of the appropriate insulin dose based on accurate identifications of food items in these object representations. For example, by accurately identifying a particular food item, the example techniques described in this disclosure may accurately quantify a degree and/or rate to which patient 12's glucose level is expected to change, enabling the titration of an amount of insulin that may be effective in reverting patient 12's glucose level back to a healthy range.

To build food library 29 to accomplish the accurate identification of any food item in the captured representations (e.g., a two-dimensional and/or a three-dimensional representation) of objects, some techniques populate food library 29 with mesh models (e.g., two-dimensional or three-dimensional mesh models) as representations of a plurality of different food items. Each mesh model uses geometric figures (e.g., triangles or other polygons) to describe contours and other components of a particular food item. If one or more processors 28 determine that a mesh model representing an object suspected to be a food item matches a stored mesh model representing an object known to be the particular food item in food library 29, one or more processors 28 may determine information identifying the object as the particular food item and output content indicative of a positive identification of that particular food item in the object's mesh model representation. Cloud 26 may have access to a number of image processing mechanisms operative to compare two representation and determine whether or to what degree the two representations depict a food item and/or its volume.

In other example techniques for building food library 29, cloud 26 may collect data sets of different representations (e.g., mesh models, images, points clouds, and/or the like) depicting known food items for use in training a machine learning model. Each object's representation may be partitioned into features and possible sub-features.

In some examples, one or more processors 28 may simplify (e.g., prune) food library 29 to include a set of mappings between particular food items and corresponding food item information and/or therapy information. Some mappings may further indicate, for each particular food item, a likely increase/decrease in patient 12's glucose level that correlates with consuming that particular food item. As an example, food library 29 may include a mapping between a specific volume (e.g., a portion size) of meat (e.g., a steak) and corresponding nutrition information for that particular food item. While there are a number of different metrics for measuring a food item's nutritional value to patient 12, one or more processors 28 may utilize specific nutritional data attributes (e.g., carbohydrate count) to estimate the likely increase/decrease in patient 12's glucose level. As another example, food library 29 may include a second mapping between the portion size of the steak and corresponding therapy information. While patient 12 may utilize any one amongst different delivery systems (e.g., a smart injection pen, a syringe, or a pump 14) for diabetes therapy, one or more processors 28 may generate the therapy information to be compatible with patient 12's delivery system. One or more processors 28, in cooperation with patient 12's delivery system, may utilize the therapy information to apply parameters directing patient's therapy, for example, by setting a treatment type, a treatment amount, recommended time(s) for delivering therapy, site(s) on patient 12 for injecting a treatment, and/or the like.

Figure 2:
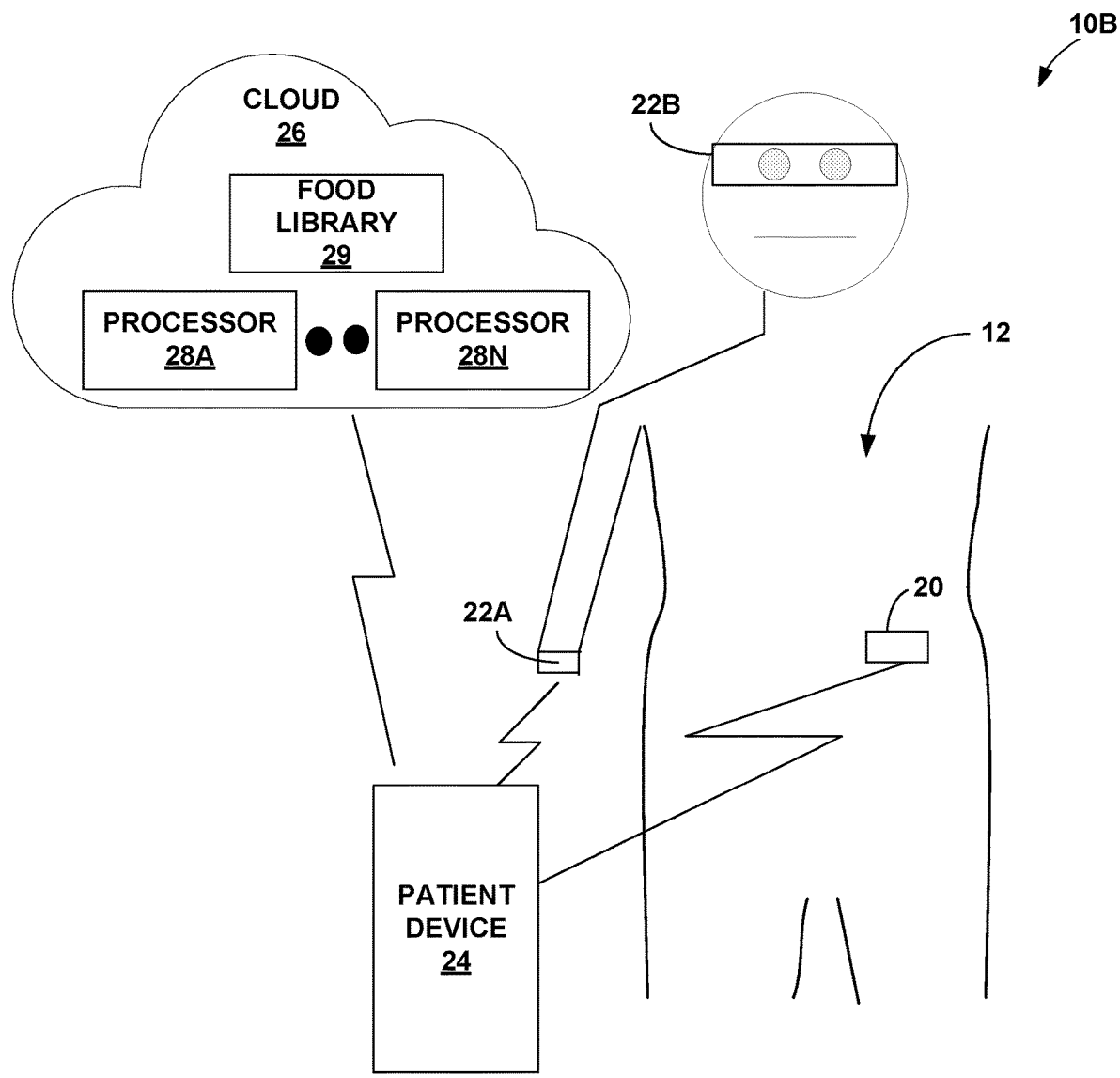
FIG. 2 is a block diagram illustrating another example system for delivering or guiding therapy dosage, in accordance with one or more examples described in this disclosure.

FIG. 2 is a block diagram illustrating another example system for delivering or guiding therapy dosage, in accordance with one or more examples described in this disclosure. FIG. 2 illustrates system 10B that is similar to system 10A of FIG. 1. However, in system 10B, patient 12 may not have insulin pump 14. Rather, patient 12 may utilize a manual injection device (e.g., an insulin pen or a syringe) to deliver insulin. For example, rather than insulin pump 14 automatically delivering insulin, patient 12 (or possible a caretaker of patient 12) may fill a syringe with insulin or set the dosage amount in an insulin pen and inject himself or herself.

As described above, wearable device(s) 22 and/or patient device 24 may be configured to determine data corresponding to one or more food items that patient 12 is eating or considering eating. In some examples, one or more processors 28 of cloud 26 may support the determination of such data by generating information identifying each particular food item (e.g., by name (e.g., steak) or by type (e.g., meat)). One or more processors 28 of cloud 26 may further generate other food item information including nutrition information (e.g., carbohydrate count) and/or volume information (e.g., portion size) for each particular food item. Using such information, one or more processors 28 may generate therapy information specifying a time, an amount, and/or a type of treatment delivery with the manual injection device. One or more processors 28 may generate a treatment schedule of manual injection times for patient 12 to follow.

To help guide patient 12 through his/her diabetes therapy, one or more processors 28 may generate (e.g., for output on an electronic display of patient device 24) content indicative of at least a portion of the above therapy information. For example, one or more processors 28 may communicate to patient device 24 the above treatment schedule of manual injection times for display to patient 12. Patient device 24 may display the treatment schedule and/or highlight a next scheduled injection of insulin (or another treatment). As described herein, patient device 24 may monitor patient 12's movements (e.g., arm movements) for gestures indicative of a manual injection, particularly at or around a time of the next scheduled injection, in order to determine whether patient 12 took his/her scheduled diabetes treatment. Upon detecting no injection at or around the time of the next scheduled injection, patient device 24 and/or one or more processors 28 may determine that patient 12 forgot and/or missed their next scheduled injection; to alert patient 12 of the possible risk to their health by not following their treatment schedule, patient device 24 may output content warning patient 12 that the next scheduled injection has not been detected.

Figure 3:
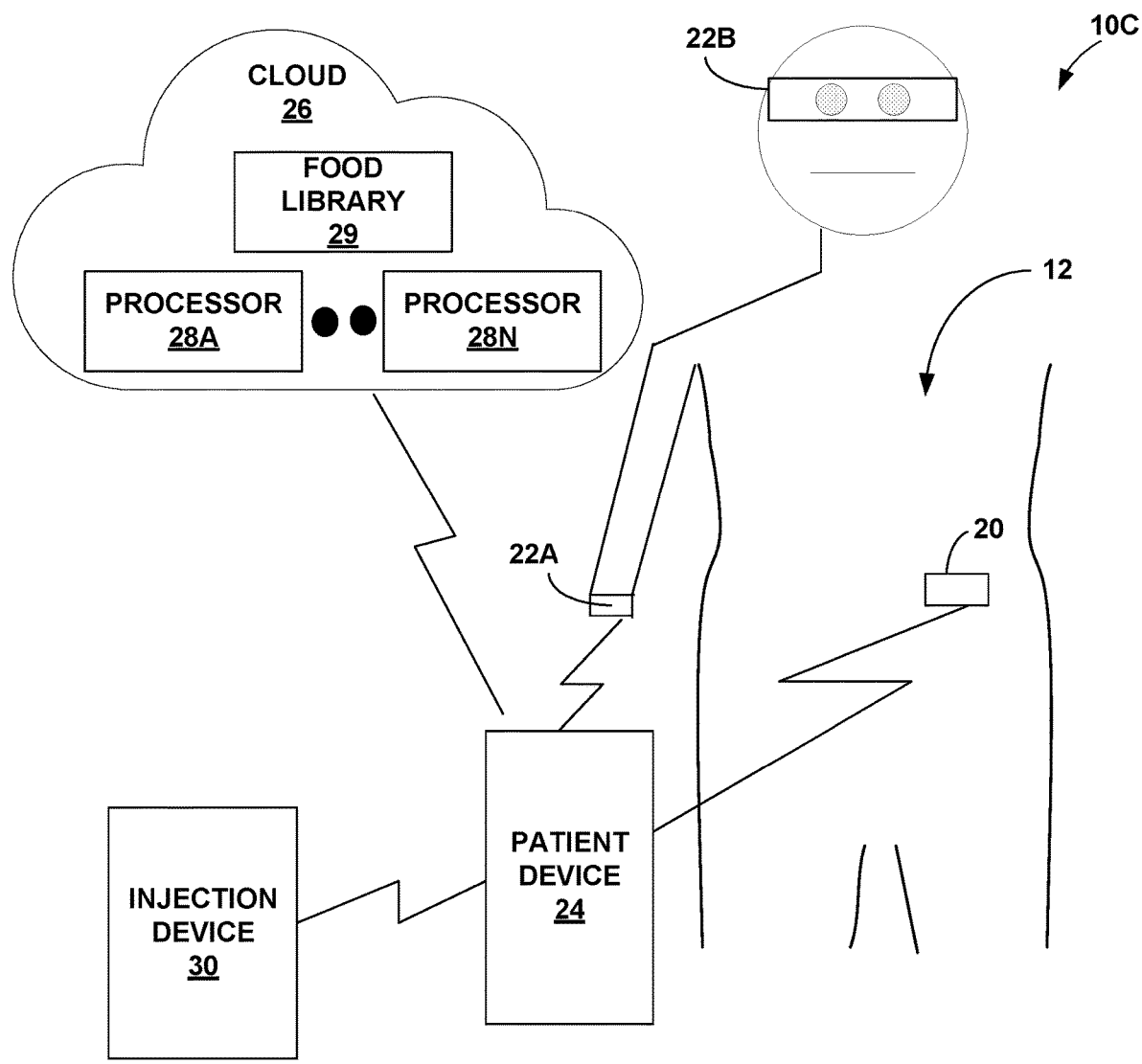
FIG. 3 is a block diagram illustrating another example system for delivering or guiding therapy dosage, in accordance with one or more examples described in this disclosure.

FIG. 3 is a block diagram illustrating another example system for delivering or guiding therapy dosage, in accordance with one or more examples described in this disclosure. FIG. 3 illustrates system 10C that is similar to system 10A of FIG. 1 and system 10B of FIG. 2. In system 10C, patient 12 may not have insulin pump 14. Rather, patient 12 may utilize injection device 30 to deliver insulin. For example, rather than insulin pump 14 automatically delivering insulin, patient 12 (or possible a caretaker of patient 12) may utilize injection device 30 to inject himself or herself.

Injection device 30 may be different than a syringe because injection device 30 may be a device that can communicate with patient device 24 and/or other devices in system 10C. Also, injection device 30 may include a reservoir, and based on information indicative of how much therapy dosage to deliver may be able to dose out that much insulin for delivery. For example, injection device 30 may automatically set the amount of insulin based on the information received from patient device 24. In some examples, injection device 30 may be similar to insulin pump 14, but not worn by patient 12. One example of injection device 30 is an insulin pen, sometimes also called a smart insulin pen. Another example of injection device 30 may be an insulin pen with a smart cap, where the smart cap can be used to set particular doses of insulin.

In some examples, injection device 30 may preset parameters for a scheduled injection to deliver an insulin dose in accordance with therapy information generated by one or more processors of the example system, such as one or more processors 28 of cloud 26. As described herein, wearable devices 22A or 22B and/or patient device 24 may determine data corresponding to one or more food items that patient 12 is eating or considering eating (e.g., a co-registered mesh model of an object suspected to be a food item), and based on that data, one or more processors 28 of cloud 26 may generate the therapy information, for example, specifying a time, an amount, and/or a type of treatment delivery with injection device 30. In some examples, based on information identifying each particular food item (e.g., by name (e.g., steak) or by type (e.g., meat)), one or more processors 28 of cloud 26 may generate other food item information including nutritional facts (and other nutrition information) and portion sizes (and other volume information) for each particular food item. Cloud 25 may maintain food library 29 to store information describing an expected impact from patient 12 consuming the one or more food items. In some examples, one or more processors 28 may estimate, based on a particular food item's carbohydrate count, an increase in patient 12's glucose level and determine an amount and/or type of diabetes treatment (e.g., insulin) to administer, for example, in order to offset the estimated increase.

If patient 12 forgets the scheduled injection, patient device 24 and/or injection device 30 may output an alert notifying patient 12 of the missed dosage and one or more processors 28 may determine whether to modify any of parameters in the therapy information in response to the missed dosage. In some examples, to account for the missed dosage, one or more processors 28 may instruct injection device 30 to adjust a current insulin level available in the reservoir, in preparation of a stronger dose. One or more processors 28 may instruct injection device 30 to change an insulin type. If the scheduled injection was during mealtime, the missed dosage may be appropriate only for mealtime; for at least this reason, injection device 30 may be directed to replace bolus insulin with basal insulin.

The above examples described insulin pump 14, a syringe, and injection device 30 as example ways in which to deliver insulin. In this disclosure, the term "insulin delivery device" may generally refer to any device used to deliver insulin. Examples of insulin delivery device include insulin pump 14, a syringe, and injection device 30. As described, the syringe may be a device used to inject insulin but is not necessarily capable of communicating or dosing a particular amount of insulin. Injection device 30, however, may be a device used to inject insulin that may be capable of communicating with other devices (e.g., via Bluetooth, BLE, and/or Wi-Fi) or may be capable of dosing a particular amount of insulin. Injection device 30 may be powered (e.g., battery powered) device, and the syringe may be device that requires no power.

Figure 4:
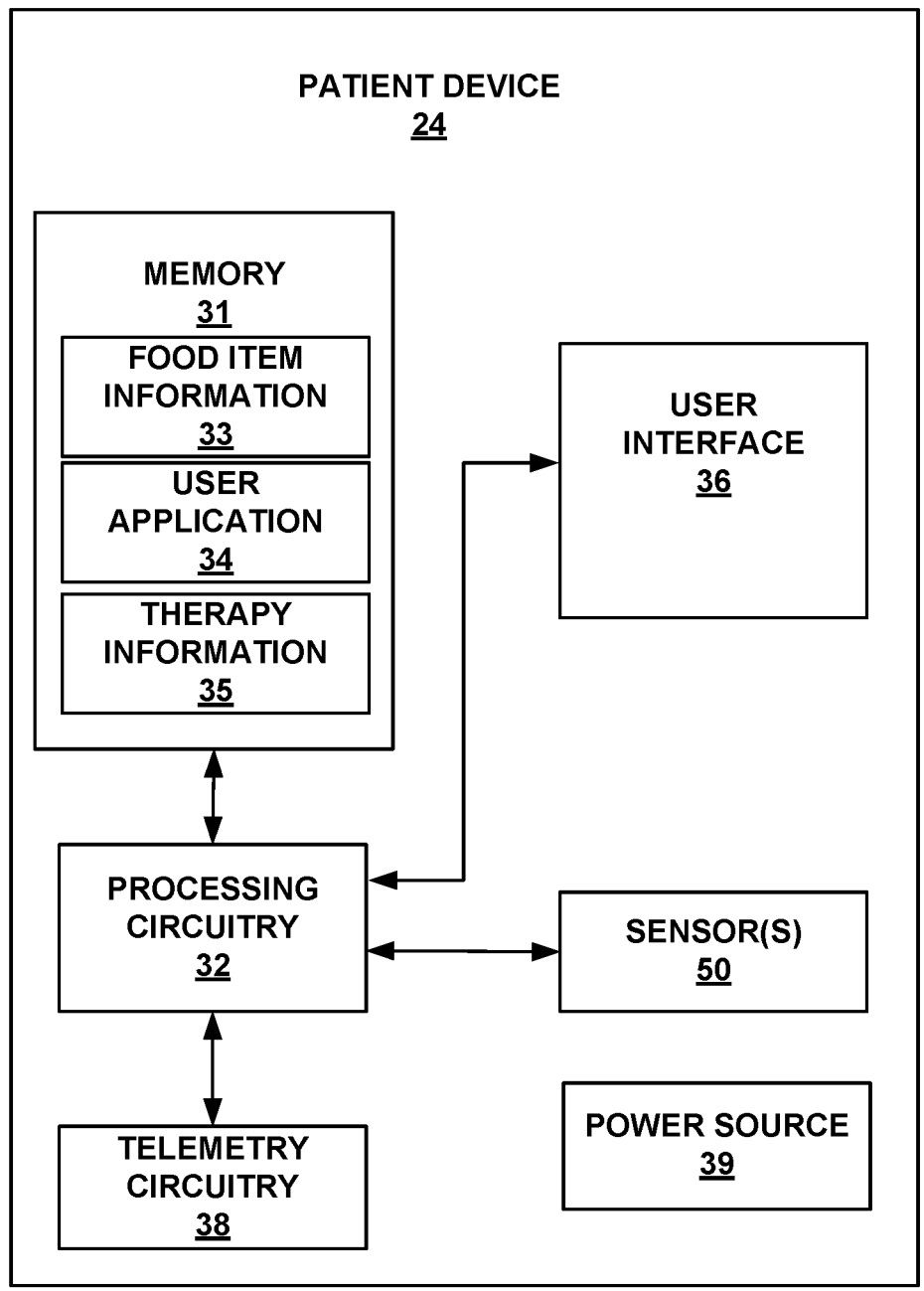
FIG. 4 is a block diagram illustrating an example of a patient device, in accordance with one or more examples described in this disclosure.

FIG. 4 is a block diagram illustrating an example of a patient device, in accordance with one or more examples described in this disclosure. While patient device 24 may generally be described as a hand-held computing device, patient device 24 may be a notebook computer, a cell phone, or a workstation, for example. In some examples, patient device 24 may be a mobile device, such as a smartphone or a tablet computer. In such examples, patient device 24 may execute an application that allows patient device 24 to perform example techniques described in this disclosure. In some examples, patient device 24 may be specialized controller for communicating with insulin pump 14.

Although the examples are described with one patient device 24, in some examples, patient device 24 may be a combination of different devices (e.g., mobile device and a controller). For instance, the mobile device may provide access to one or more processors 28 of cloud 26 through Wi-Fi or carrier network and the controller may provide access to insulin pump 14. In such examples, the mobile device and the controller may communicate with one another through Bluetooth or BLE. Various combinations of a mobile device and a controller together forming patient device 24 are possible and the example techniques should not be considered limited to any one particular configuration.

As illustrated in FIG. 4, patient device 24 may include a processing circuitry 32, Memory 31, user interface 36, telemetry circuitry 38, and power source 39. Memory 31 may store program instructions that, when executed by processing circuitry 32, cause processing circuitry 32 to provide the functionality ascribed to patient device 24 throughout this disclosure.

In some examples, memory 31 of patient device 24 may store a plurality of attributes, such as a food item type, a carbohydrate count, number of servings, a portion size, a calorie count, etc., as food item information 33. For each food item that has been eaten or is about to be eaten, example attributes in general may identify that food item (e.g., by name or type) and provide at least one of nutrition information or volume information. Processing circuitry 32 (e.g., via user interface 36) may output various content indicative of at least one of the attributes stored in memory 31. Processing circuitry 32 (e.g., via user interface 36) may receive input specifying any of the above-mentioned attributes and/or other attributes of the plurality of attributes stored in memory 31.

In some examples, user application may include a computer program configured to generate a graphical user interface (GUI) and execute logic that provides functionality corresponding to guiding patient 12's therapy, for example, by supporting the proactive monitoring of patient 12's food consumption with access to food library 29 and dynamic adjustment of the patient's 12's treatment type, amount, and/or delivery time. User application 34 may be mobile application configured to run on a mobile device (e.g., a smartphone) and assist patient 12 in capturing representations of food items and accessing services provided by cloud 26. In some examples, user application 34 on behalf of patient 12 may submit the representations of food items and request that one or more processors 28 analyze these representations and (if needed) modify patient 12's current diabetes therapy as codified in therapy information 35.

In some examples, memory 31 of patient device 24 may store a plurality of parameters, such as amounts of insulin to deliver, target glucose level, time of delivery etc., as therapy information 35. Processing circuitry 32 (e.g., through telemetry circuitry 38) may output the parameters stored in memory 31 to insulin pump 14 or injection device 30 for delivery of insulin to patient 12. Processing circuitry 32 (e.g., via user interface 36) may output various content indicative of the parameters stored in memory 31. In some examples, processing circuitry 32 may execute a notification application, stored in memory 31, that outputs notifications to patient 12, such as notification to take insulin, amount of insulin, and time to take the insulin, via user interface 36. The notification application may communicate similar notifications to a device operated by patient 12's caregiver to which an electronic display may present these notifications. In other examples, the notification application may output content indicative of notifications to patient 12, such as notification to take insulin, amount of insulin, and time to take the insulin, via user interface 36.

One or more sensor(s) 50 may include any available sensing technology such as a camera sensor capable of providing two-dimensional data and/or a LiDAR sensor capable of providing three-dimensional data in any format including point clouds—which may alternatively be referred to as "point cloud data" or "point cloud data sets" in the present disclosure. The LiDAR sensor may produce LiDAR sensor data including point cloud data in the format of (x, y, z, r) where x, y, and z are 3D coordinates and r is reflectivity (the intensity of the reflected laser light). A LiDAR sensor may generate point clouds/maps to represent a region in three-dimensional space where each three-dimensional data cube (e.g., voxel) maps to a two-dimensional area in a camera image of the above-mentioned image data. In some examples, the three-dimensional data and the image data are captured simultaneously, concurrently, or serially by one or more sensor(s) 50. As described herein, points of the point clouds form contours of an object (or a specific feature) of interest, and an example system may co-register these representations by correlating or aligning those points of the point cloud data with the image data; for example, this correlation may be accomplished as a projection of the point cloud data to a specific region of the image data. Instead of processing all the point clouds, example system processes (e.g., correlates) only the portion that maps to the specific region of the image data, reducing overall resource consumption (e.g., fewer processor cycles/capacities, fewer memory blocks/storage units, etc.) and resource requirements (e.g., less processing power, less memory/storage space, etc.).

In some examples, one or more processors 28 may simplify (e.g., prune) food library 29 to include a set of mappings between particular food items and corresponding food item information and/or therapy information. In some examples, each mapping may provide information for determining when a next insulin dose is to be taken. Some mappings may further indicate, for each particular food item, a likely increase/decrease in patient 12's glucose level that correlates with consuming that particular food item. In some examples, one or more processors 28 may determine a rate that particular food item decreases/increases the patient's glucose level based on information provided by insulin pump 14 and/or sensor 20 and/or information provided by food library 29. For the particular food item or any food item(s) of a specific food type, one or more processors 28 may mathematically combine sensed measurements (e.g., glucose level readings) with corresponding volume information (e.g., discrete portion sizes or a continuous volumetric function) to determine an approximate rate or rates at which, for example, patient 12's glucose level is expected to change. It is well known that foods having a blend of carbohydrates, fats, and proteins will raise blood sugar more slowly than foods that are predominately carbohydrates. To illustrate by way of example, most forms of pizza, regardless of how many slices (e.g., portion sizes), are rich in carbohydrates and fats (e.g., unsaturated fats) and contain considerably above normal amounts of each. Considering each slice to be a discrete portion size, some examples may compute the rate at which patient 12's glucose level changes as a ratio between an expected increase or decrease (e.g., in mg/dL or mmol/L where mmol represents a millimole) and a number of slices. Because of the high fat content in a single pizza slice and especially in a large portion size (e.g., a substantial number of slices or whole pies), patient 12 may digest one or more pizza slices slowly, resulting in a steady and eventually prominent increase in patient 12's glucose level. To overcome or mitigate such an increase, one or more processors 28 may modify patient 12's therapy information 35 to deliver, at a next scheduled treatment, a partial dose of bolus insulin before starting a meal event and then, a remainder of the dose of bolus insulin at least an hour after concluding the meal event. By doing so, one or more processors 28 may improve upon an effectiveness of patient 12's diabetes treatments (e.g., treatment schedule). This may be because patient 12's next treatment (as modified) accounts for the carbohydrates and/or the prolonged digestion process, thereby improving patient 12's diabetes management and health.

In some examples, food library 29 may include a mapping between a specific volume (e.g., a portion size) of meat (e.g., a steak) and corresponding nutrition information for that particular food item. While there are a number of different metrics for measuring a food item's nutritional value to patient 12, one or more processors 28 may utilize specific nutritional data attributes (e.g., carbohydrate count) to estimate the likely changes (e.g., increase or decrease) in patient 12's glucose level. As another example, food library 29 may include a second mapping between the portion size of the steak and corresponding therapy information. While patient 12 may utilize any one amongst different delivery systems (e.g., a smart injection pen, a syringe, or a pump 14) for diabetes therapy, one or more processors 28 may generate the therapy information to be compatible with patient 12's delivery system. One or more processors 28, in cooperation with patient 12's delivery system, may utilize the therapy information to apply parameters directing patient's therapy, for example, by setting a treatment type, a treatment amount, recommended time(s) for delivering therapy, site(s) on patient 12 for injecting a treatment, and/or the like.

In some examples, one or more processors 28 of cloud 26 populates one or both of food item information 33 and therapy information 35 as stored in memory 31 of patient device 24. For any given food item including the particular food item described above, user application may download (e.g., from food library 29 of cloud 26) mappings between the given food item and attributes corresponding to nutrition content of that food item, attributes corresponding to measurement(s) of that food item's volume, parameters corresponding to controlling patient 12's diabetes therapy (e.g., by determine a next treatment amount, type, and/or delivery time), and other data. In some examples, the downloaded mappings may further include data (e.g., feature data) for accurate identification of the given food item in an object's representation. If patient 12 provides (in advance) the particular food item's identity, the data for accurate identification may include various indicia to confirm the object's purported identity as the particular food item. Example features may include eigenvectors, eigenvalues, surface texture gradients, and/or temperature gradients, and any combinations of these features may identify the particular food item in the object's representation.

Memory 31 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 32 can take the form one or more microprocessors, DSPs, ASICs, FPGAs, programmable logic circuitry, or the like, and the functions attributed to processing circuitry 32 herein may be embodied as hardware, firmware, software or any combination thereof.

User interface 36 may include a button or keypad, lights, a speaker for voice commands, and a display, such as a liquid crystal (LCD). In some examples the display may be a touchscreen. As discussed in this disclosure, processing circuitry 32 may present and receive information relating to therapy via user interface 36. For example, processing circuitry 32 may receive patient input via user interface 36. The patient input may be entered, for example, by pressing a button on a keypad, entering text, or selecting an icon from a touchscreen. The patient input may be information indicative of food that patient 12 eats, such as for the initial learning phase, whether patient 12 took the insulin (e.g., through the syringe or injection device 30), and other such information.

Telemetry circuitry 38 includes any suitable hardware, firmware, software or any combination thereof for communicating with another device, such as cloud 26, insulin pump 14 or injection device 30, as applicable, wearable devices 22A or 22B, and sensor 20. Telemetry circuitry 38 may receive communication with the aid of an antenna, which may be internal and/or external to patient device 24. Telemetry circuitry 38 may be configured to communicate with another computing device via wireless communication techniques, or direct communication through a wired connection. Examples of local wireless communication techniques that may be employed to facilitate communication between patient device 24 and another computing device include RF communication according to IEEE 802.11, Bluetooth, or BLE specification sets, infrared communication, e.g., according to an IrDA standard, or other standard or proprietary telemetry protocols. Telemetry circuitry 38 may also provide connection with carrier network for access to cloud 26. In this manner, other devices may be capable of communicating with patient device 24.

Power source 39 delivers operating power to the components of patient device 24. In some examples, power source 39 may include a battery, such as a rechargeable or non-rechargeable battery. A non-rechargeable battery may be selected to last for several years, while a rechargeable battery may be inductively charged from an external device, e.g., on a daily or weekly basis. Recharging of a rechargeable battery may be accomplished by using an alternating current (AC) outlet or through proximal inductive interaction between an external charger and an inductive charging coil within patient device 24

Figure 5:
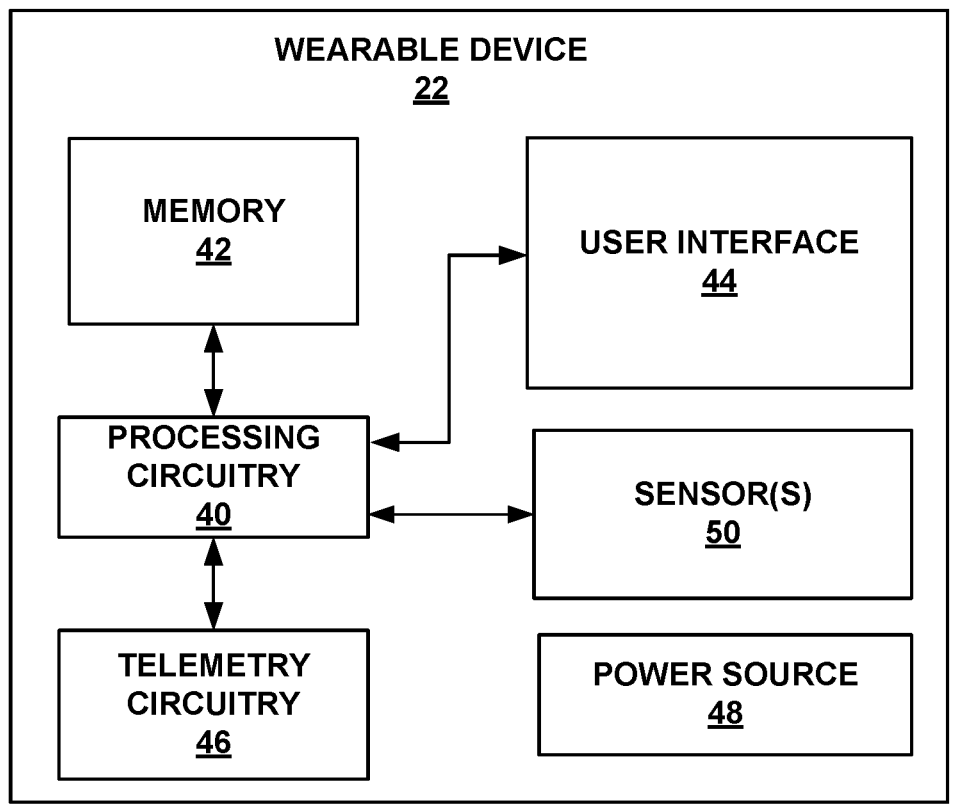
FIG. 5 is a block diagram illustrating an example of a wearable device, in accordance with one or more examples described in this disclosure.

FIG. 5 is a block diagram illustrating an example of a wearable device, in accordance with one or more examples described in this disclosure. As illustrated, wearable device 22 includes processing circuitry 40, memory 42, user interface 44, telemetry circuitry 46, power source 48, and sensor(s) 50. Processing circuitry 40, memory 42, user interface 44, telemetry circuitry 46, and power source 48 may be similar to processing circuitry 32, Memory 31, user interface 36, telemetry circuitry 38, and power source 39 of FIG. 3, respectively. Wearable device 22 represents any wearable device that is described herein or conceivable in view of the present disclosure. FIGS. 1-3 depict wearable device 22A or 22B of which a smart watch and smart glasses are respective representative examples.

One or more sensor(s) 50 may include any available (image) sensing technology such as a camera capable of providing two-dimensional data and/or a LiDAR sensor capable of providing three-dimensional data in any format including point clouds—which may alternatively be referred to as "point cloud data" or "point cloud data sets" in the present disclosure. The LiDAR sensor may produce LiDAR sensor data including point cloud data in the format of (x, y, z, r) where x, y, and z are 3D coordinates and r is reflectivity (the intensity of the reflected laser light). LiDAR sensor may generate point clouds to represent a region in three-dimensional space where each three-dimensional data cube (e.g., voxel) maps to a two-dimensional area in a camera image of the above-mentioned image data. In some examples, the three-dimensional data and the image data are captured simultaneously, concurrently, or serially by one or more sensor(s) 50. As described herein, points of the point clouds form contours of an object (or a specific feature) of interest, and an example system may co-register these representations by correlating or aligning those points of the point cloud data with the image data; for example, this correlation may be accomplished as a projection of the point cloud data to a specific region of the image data. Instead of processing all the point clouds, example system processes (e.g., correlates) only the portion that maps to the specific region of the image data, reducing overall resource consumption (e.g., fewer processor cycles/capacities, fewer memory blocks/storage units, etc.) and resource requirements (e.g., less processing power, less memory/storage space, etc.). Example features of interest may include eigenvectors, eigenvalues, surface texture gradients, and/or temperature gradients, and any combinations of these features may identify the particular food item in the object's representation.

Inertial measurement units are other examples of sensor(s) 50 and may include gyroscopes and/or various components to determine a pitch-roll-yaw, and x-y-z coordinate of wearable devices 22A or 22B. In some examples, inertial measurement units may be considered as a six-axis inertial measurement unit. For example, inertial measurement units may couple a 3-axis accelerometer with a 3-axis gyroscope. The accelerometer may measure linear acceleration, while the gyroscope may measure rotational motion. Processing circuitry 40 may be configured to determine one or more movement characteristics based on values from inertial measurement units. For example, processing circuitry 40 may determine based on values from inertial measurement units if patient 12 is moving his or her arm upwards, downwards, leftwards, rightwards, forwards, backwards, or some combination, including values related to frequency, amplitude, trajectory, position, velocity, acceleration, and/or pattern of movement. Processing circuitry 40 may determine based on values from inertial measurement units orientation of the arm of patient 12, such as whether the back of the hand or the front of the hand is facing patient 12, or if a side of the hand is facing patient 12, such that the thumb is facing patient 12 and the side of the index finger is visible.

As one example, when patient 12 is holding chopsticks to eat, patient 12 may orient his or her wrist in a particular manner, which may be different than if patient 12 is holding a sandwich. The frequency of patient 12 moving his or her arm from a position where he or she is reaching food to a position where he or she is placing food in mouth may be different for different types of food. For example, the frequency and pattern of movement of eating with a fork may be different than eating with a spoon or a knife and fork, which may be different than eating with hands, like a sandwich or pizza. For all of these different food items, there may be a difference in the movement characteristics, and different output values from inertial measurement units. However, for all of the movement characteristics, one or more processors (including processing circuitry 40 in some examples) may be configured to determine that patient 12 is eating. In some examples, the one or more processors may use contextual information (e.g., time of day, location, detection of a pre-meal bolus) to determine that patient 12 is eating, as described above.

Inertial measurement units may output such information (e.g., pitch-roll-yaw and x-y-z coordinates) of the arm of patient 12 to processing circuitry 40. Telemetry circuitry 46 may then output the information from processing circuitry 40 to patient device 24. Patient device 24 may forward the information to one or more processors 28 that can use the information to determine if patient 12 is eating (e.g., if a meal event is occurring).

Figure 6:
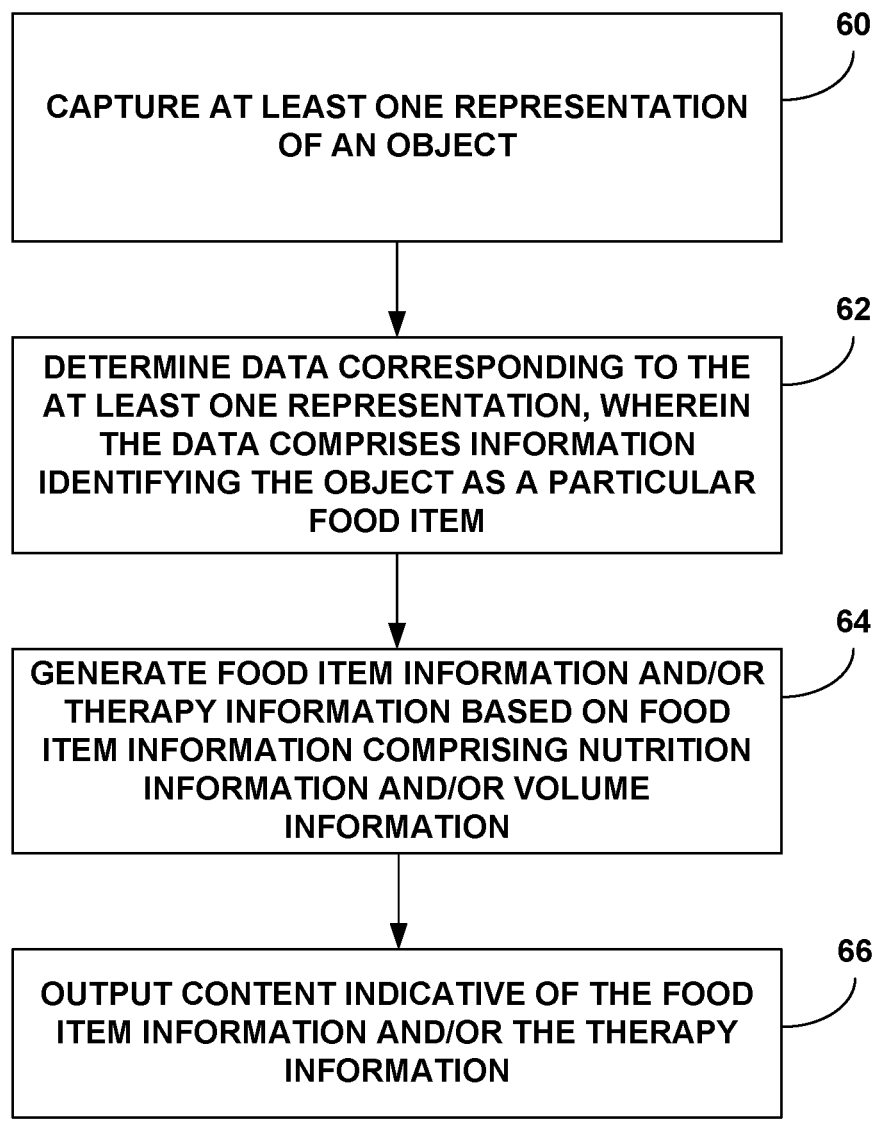
FIG. 6 is a flow diagram illustrating an example operation for delivering or guiding therapy dosage, in accordance with one or more examples described in this disclosure.

FIG. 6 is a flow diagram illustrating an example operation for delivering or guiding therapy dosage, in accordance with one or more examples described in this disclosure. Example operation may be performed on a patient (e.g., patient 12) using that patient's device(s), which includes one or more of wearable devices 22A or 22B, patient device 24, and/or cloud 26 as described in FIGS. 1-5. FIG. 6 is described with respect to one or more processors. The one or more processors may be one or more processors 28 of cloud 26, one or more processors of patient device 24 (e.g., processing circuitry 32), one or more processors of wearable devices 22A or 22B (e.g., processing circuitry 40), one or more processors of insulin pump 14 (if available), one or more processors of injection device 30 (if available), or any combination thereof.

As described herein, a patient (e.g., patient 12) may benefit from wearable devices 22A or 22B, patient device 24, and/or cloud 26 performing the example operation, for example, by proactive monitoring of the patient's food consumption and (if needed) adapting the patient's diabetes therapy delivery. While the patient may have access to any combination of wearable devices 22A or 22B, patient device 24, and/or cloud 26, FIG. 6 is described with respect to the patient's device(s) (e.g., patient device 24 or a similar device). User application 34 of patient device 24 of which the patient may also be a user, supports the example operation, for example, by coordinating the patient's diabetes therapy delivery, for example, in cooperation with cloud 26. Cloud 26 may support the example operation, for example, by providing the patient's devices with food library 29 access and computing services, for example, services enabling accurate estimation of a particular food item's impact on the patient's glucose level and accurate determination of the particular food item's nutritional content and/or portion size or volume. If a food item's identity (e.g., name or type) is not known or provided (e.g., by the patient), the example operation may leverage services enabling accurate identification of any food item that the patient is eating or is about to eat. Some services leverage machine learning techniques that use mesh models of different food items for training a machine learning model to accurately identify one or more food items in a mesh model that may or may purport to be any particular food item.

In general, the example operation may commence at point such as when the one or more processors capture at least one representation of an object (60). As described herein, the patient may be considering eating a food item or currently eating that food item. In the patient's device(s), the one or more processors instruct one or more sensors (e.g., imaging sensors) may capture the at least one representation, for example, one or more two-dimensional representations (e.g., pixelized image data) of the food item and/or one or more three-dimensional representations (e.g., point cloud data, voxelized image data) of the food item. The one or more processors may apply a co-registration mechanism to align the two-dimensional and three-dimensional representations and, in some example, generate a combined two-dimensional or three-dimensional representation.

The one or more processors may determine data corresponding to the least one representation of the object wherein the data comprises information identifying the object as a particular food item (62). As described herein, the patient via the patient's device(s) may provide cloud 26 the particular food item's name and/or type, for example, by entering such information into user application 34 and accessing food library 29. In some examples, the patient's device(s) may provide feature data corresponding to the least one representation of the object and/or the combined two-dimensional or three-dimensional representation to cloud 26 where the machine learning model is configured to determine whether the object actually is the particular food item, for example, in confirmation of the patient's input into user application 34. Feature data may specify values for a number of example features that may be found in a mesh model of the particular food item, such as eigenvectors, eigenvalues, surface texture gradients, and/or temperature gradients. In one example, a Thermal Imaging IR device (e.g., smartphone) attachment may capture an example temperature gradient of a food item on patient device 24 and/or wearable device 22.

As described herein, a smart watch, a pair of smart glasses, or another example of wearable device 22 may provide the data corresponding to the least one representation of the object to patient device 24. FIGS. 1-3 depict wearable devices 22A and 22B and in some examples, one or both of these devices may support the identification of the object as the particular food item. For example, wearable device 22B may include one or more imaging sensors configured to capture two-dimensional or three-dimensional representations of objects. In addition, wearable device 22B may utilize the one or more imaging sensors to identify various patient actions involving the object, such as the patient eating and/or consuming the object. Wearable device 22B and/or patient device 24 may determine, based on data captured by the one or more imaging sensors, that the patient consumed the object and may proceed to identify the object as the particular food item. In this manner, the example operation may consider such data as confirmation of the patient's consumption and have the patient's diabetes therapy modified without considering a possibility that the patient did not actually consume the object and therefore, any estimate of the patient's glucose level will be inaccurate.

The one or more processors may generate food item information and/or therapy information based on the food item information (64). The food item information may include nutrition information and/or volume information for the particular food item that the patient is eating or about to eat. In some examples, the food item information includes attributes describing the particular food item including the particular food item's name (e.g., a steak) and/or type (e.g., meat), content (e.g., a carbohydrate count, a caloric count, a portion size (or any volume measurement), fat/proteins in grams), and/or the like. In some examples, the therapy information including parameters controlling the patient's therapy including the therapy's treatment schedule, amount, and/or type. The one or more processors may utilize one or more of the above-mentioned attributes to determine one or more of the above-mentioned parameters of the therapy information.

The one or more processors may output content indicative of the food information food item information (66). In some examples, the patient may be scheduled for a treatment (e.g., an insulin dose) from one of the delivery systems mentioned herein but the patient may have or be consuming a food item likely to increase the patient's glucose level to an extent that the patient's current therapy is no longer effective or less effective. The one or more processors may determine an appropriate treatment amount and/or type and then, modify the patient's scheduled treatment. To the patient's benefit, the modification may be accomplished by the one or more processors configuring injection device 30 or insulin pump 14 to prepare a correct dosage of insulin at the appropriate treatment amount, type, and/or time.

In one example, the patient's mobile device (e.g., smartphone) utilizes a Diabetes Management Application (e.g., user application 34) to capture an image the object suspected to be a food item. The image may be digitized into 3D image mesh model data. Then, the digitized 3D image mesh model data is transmitted to cloud 26 where one or more processors 28 generates co-registered 3D image mesh models of the digitized food item for identifying a matching pre-stored food item image mesh models (which is retrieved from food library 29). The co-registered model mesh image is transmitted to the Diabetes Management App on the smartphone, which displays matching volume and portion size nutrition information (e.g., a carbohydrate count) retrieved form food library 29.

Figure 7:
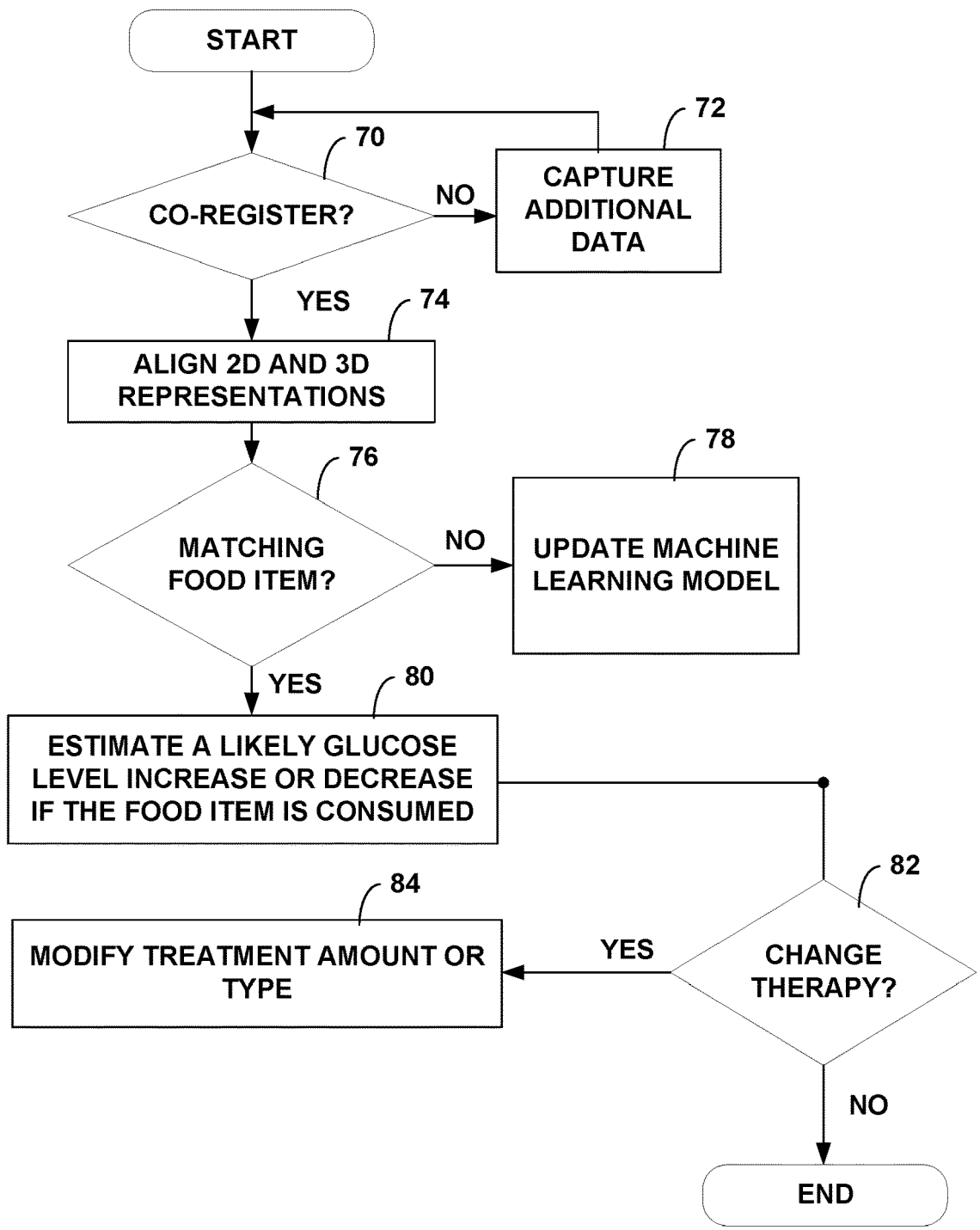
FIG. 7 is a flow diagram illustrating an example operation for delivering or guiding therapy dosage, in accordance with one or more examples described in this disclosure.

FIG. 7 is a flow diagram illustrating a second example operation for delivering or guiding therapy dosage, in accordance with one or more examples described in this disclosure. Similar to FIG. 6, FIG. 7 is described with respect to one or more processors and a patient. The one or more processors may be one or more processors 28, one or more processors of patient device 24 (e.g., processing circuitry 32), one or more processors of wearable devices 22A or 22B (e.g., processing circuitry 40), one or more processors of insulin pump 14 (if available), or any combination thereof. The patient may be a diabetes patient similar to patient 12 and the patient's device(s) include one or more of wearable devices 22A or 22B, patient device 24, and/or cloud 26 and possible one or more additional devices. The patient may be a user of user application 34 but user application 34 is not required for this example operation.

As illustrated in FIG. 7, the one or more processors may commence the second example operation by determining whether to co-register two or more representations of an object suspected to be a food item including one or more two-dimensional images, one or more two-dimensional mesh models and one or more three-dimensional mesh models (70). Based on determining not to co-register the object's representations (NO of 70), the one or more processors may proceed to capture additional data (72). The one or more processors may use the additional captured data to more accurate predict which food item(s) do the mesh models depict. Additional images may be required if the food item corresponds to a complex mesh model. Successful co-registration may require additional LiDAR data, for example, to correct an inaccurate polygon in the mesh model, add features (e.g., fine-grained features), increase the mesh model's resolution, and/or the like. As described herein, the patient's devices (e.g., as directed by the one or more processors) may operate an internal or external sensor (e.g., an imaging sensor) to capture the additional data corresponding to the object's representations. In some examples, the one or more processors may periodically capture the additional data and update the representations for the co-registration. As an option, the one or more processors may communicate a control directive causing the patient's devices to output a request for input, such as a query for the object's identity as a particular food item.

To illustrate by way of example, the patient may open user application 34 on patient device 24 and using sensors in wearable devices 22A or 22B and/or patient device 24, capture a 3D point-cloud image (e.g., map) and a 2D image of an object suspected to be a food item. In some examples, wearable devices 22A or 22B and/or patient device 24 may capture these images simultaneously (or near-simultaneously/concurrently) in order to capture near identical 2D and 3D object representations for both images. In some examples, wearable devices 22A or 22B and/or patient device 24 may be configured to generate a 2D mesh model and a 3D mesh model from the 2D camera image and the 3D LiDAR image, respectively. Each mesh model captures points or point clouds detailing a representation of the object in space.

Based on determining to co-register the object's representations (YES of 70), the one or more processors may align the two-dimensional representations and three-dimensional representations (74). In some examples, these two-dimensional representations and three-dimensional representations may include additional data capture at step 72. In some examples, the aligned mesh models may include an aligned object in a same coordinate system and orientation. In this manner, the one or more processors may map color data of a two-dimensional image to a volume within the object's geometry in the three-dimensional mesh model.

The one or more processors may proceed to determine whether the aligned representations match a particular food item (76). In some examples, the one or more processors (e.g., one or more processors 28 of cloud 26) may compare co-registered 2D/3D mesh model data and feature data (e.g., eigenvectors, eigenvalues, surface texture gradients, and temperature gradients) with stored data (e.g., pre-stored features and other indicia) indicative of a particular food item in food library 29. Based on results of the above comparison, the one or more processors may generate a 3D mesh model of the particular food item.

The one or more processors may compare nutrition and/or volume information for the particular food item to pre-stored nutrition and/or volume information (e.g., X, Y, Z coordinate data including roll, pitch, and yaw information; portion size; carbohydrate count; calorie count; and other nutritional data) in food library 29 and based on the comparison results, determine an accurate estimation of the particular food item's nutritional value and/or portion size. The one or more processors may then use the particular food item's nutritional value and/or portion size to determine an amount and/or rate that the glucose level is likely to change if/when the patient consumes the particular food item. In some examples, one or more processors 28 perform the comparison while in other examples, patient device 24 may download the nutrition and/or volume information from food library 29. In the background, user application 34 of patient device 24 may collect (e.g., in memory cache) historical and trace data of the particular food item, which enables faster and more efficient retrieval of future reference food items. In some examples of food library 29, one or more processors 28 may provide patient device 24 at least a portion of the machine learning model for user application 34 to use as a local copy of that model. Over time, patient device 24 may update that local copy (e.g., with additional training) to enable a faster temporal response.

Based on determining that the aligned representations do not match any one of a plurality of pre-registered food items (NO of 76), the one or more processors may update a machine learning model (e.g., food library 29) (78). As described herein, the machine learning model may be configured to identify the particular food item in the object's representations. The machine learning model may be further configured to determine the particular food item's nutritional content and/or volume based on the aligned mesh model(s).

Based on determining that the aligned representations match at least one of the pre-registered food items (YES of 76), the one or more processors may estimate a likely glucose level increase or decrease if the particular food item is consumed (80). As described herein, the particular food item's nutritional content may negatively affect the patient's glucose level, for example, by cause that glucose level to increase to level that renders the patient's current therapy ineffective or less effective. The one or more processors may determine whether to change the patient's therapy (82). Based on determining that the patient's therapy is to be changed (YES of 82), the one or more processors may modify a treatment amount or type to more effective amount or type (84). In some instances, the modification corrects a diabetes therapy that is inappropriate for the patient's actual diet. The one or more processors may terminate processes in support of the second example operation such that the second example operation ends. Based on determining not to change the patient's current therapy (NO of 82), the second example operation also ends.

To demonstrate by way of a recent meal event, the one or more processors may execute the example second operation illustrated in FIG. 7 in response to detecting the patient consuming food items consisting of: 1) a protein portion (e.g., meat), 2) starchy and/or green vegetable portion, 3) pasta or bread portion, and 4) a dessert portion. The one or more processors, in accordance with the example second operation, may capture one or more 3D representations (e.g., mesh model) and use those representations to determine a volume of each food item or group of food items in the meal event.

If the one or more processors cannot identify an individual food item in 3D representation, the one or more processors may group food items together to form a composite food item (e.g., soup) that, in some instances, may also have a regular volume. For instance, while it may be possible to segregate some types of vegetables (e.g., asparagus) in the vegetable portion of the meal event, for other vegetable types (e.g., spinach), it may be difficult to segregate individual ones; to mitigate this difficulty, the one or more processors may capture a representation of a group of vegetables in most (if not all) of the vegetable portion and consider that group to be single food item for determining volume information and/or nutrition information. The captured representation for that group may indicate a more simplified volume to determine than a representation of an individual vegetable. Instead of determining a volume of a single spinach leaf, the one or more processors may determine the volume of spinach leaves collected into a hemisphere or any volume that is less complicated to determine.

In some examples, the patient may combine two or more food items. For example, the patient may combine the meat portion, the vegetable portion, and/or the pasta or bread portion with a liquid to form a soup. Most soups have the meat portion, the vegetable portion, and/or the pasta or bread portion suspended in the liquid, allowing the one or more processors to accurately identify individual food items. For some soups, the one or more processors may capture a 3D mesh model, identify (e.g., and enumerate) each identifiable food item, and then, determine a volume of the entire liquid suspension. Based on a composition of food items in a particular soup, the one or more processors may determine nutrition information for the particular soup by combining each food item's nutritional content by estimated volume and/or weight—possibly including the liquid's nutritional content. Instead of the liquid suspension, some soups dissolve the meat portion, the vegetable portion, and/or the pasta or bread portion; in some examples, the one or more processors may estimate each food item by original weight and/or volume. This information may be provided via user input. Other example, combinations include casseroles, stews, chili, omelet, sandwich, hamburger, etc.

Assuming food library 29 includes a well-trained and accurate machine learning model, the example second operation may have the one or more processors leverage that model for identifying a food item in a 3D representation and determining that food item's volume and/or nutritional content to the benefit of the patient. Each food item in the meal event may contribute to an overall carbohydrate count for the patient. Upon determining each food item's contribution of carbohydrates (if any) and appropriately calibrating that patient's diabetes therapy, for example, by titrating a next dosage of insulin based on that carbohydrate determination. If the patient has a manual injection device (e.g., a syringe), the one or more processors may output data indicating the next dosage to the patient (e.g., via a mobile device such as patient device 24). If the patient has an insulin smart pen device, an insulin pen with a smart cap, or another example of injection device 30, the one or more processors may output data indicating the next dosage to injection device 30 and, in turn, injection device 30 prepares the next dosage (if possible). If the patient has an insulin delivery device such as an example of insulin pump 14, the one or more processors may output data indicating the next dosage to the insulin delivery device, which may or may not automatically administer to the patient.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including one or more processors 28 of cloud 26, one or more processors of patient device 24, one or more processors of wearable devices 22A or 22B, one or more processors of insulin pump 14, or some combination thereof. The one or more processors may be one or more integrated circuits (ICs), and/or discrete electrical circuitry, residing in various locations in the example systems described in this disclosure.

The one or more processors or processing circuitry utilized for example techniques described in this disclosure may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. The processors or processing circuitry may include arithmetic logic units (ALUs), elementary function units (EFUs), digital circuits, analog circuits, and/or programmable cores, formed from programmable circuits. In examples where the operations of the processors or processing circuitry are performed using software executed by the programmable circuits, memory accessible by the processors or processing circuitry may store the object code of the software that the processors or processing circuitry receive and execute.

Various aspects of the disclosure have been described. These and other aspects are within the scope of the following claims.

What is claimed is:

1. A system for therapy delivery for diabetes treatment, the system comprising:
   one or more sensors configured to capture a representation of an object; and processing circuitry configured to:
   determine data corresponding to the representation of the object, wherein the data comprises information identifying the object as a particular food item;
   generate food item information based on the information identifying the object as the particular food item, wherein the food item information comprises at least one of nutrition information or volume information of the particular food item;

determine that the nutrition information or the volume information of the particular food item exceeds a threshold by accessing a food library that defines the threshold;

predict the patient's glucose level will rise based on the nutrition information or the volume information of the particular food item exceeds the threshold;

responsive to determining the nutrition information or the volume information of the particular food item exceeds the threshold, generate therapy information for a patient based on the food item information and the prediction the patient's glucose level will rise based on the determination the nutrition information or the volume information of the particular food idem exceeds the threshold, wherein generating the therapy information comprises determining at least an insulin type and an insulin dosage based on the food item information;

output content indicative of at least one of the therapy information or the food item information; and automatically administer insulin to the patient in accordance with the insulin type and the insulin dosage, wherein the insulin type comprises at least one of basal insulin or bolus insulin, wherein administration of the insulin to the patient corresponds to the diabetes treatment by causing the glucose level of the patient to lower to within a predetermined range.

2. The system of claim 1 further comprising a wearable device configured to perform at least one of generating at least a portion of the data corresponding to the representation of the object or generating data indicating consumption of the object by the patient.

3. The system of claim 1, wherein to generate food item information, the processing circuitry is further configured to generate the food item information based on a machine learning model, wherein the machine learning model is trained to map the food item information to feature data corresponding to at least one of a three-dimensional or a two-dimensional representation of the object.

4. The system of claim 1, wherein to determine the data corresponding to the representation of the object, the processing circuitry is further configured to generate data corresponding to at least one of a three-dimensional representation or a two-dimensional representation of the object.

5. The system of claim 1, wherein to generate food item information, the processing circuitry is further configured to generate a mesh model of the object and based on the mesh model, determine which one amongst a plurality of food items corresponds to the object.

6. The system of claim 1, wherein to generate food item information, the processing circuitry is further configured to align a three-dimensional mesh model of the object and a two-dimensional mesh model of the object to generate a co-registered mesh model.

7. The system of claim 1, wherein to output, for display on an electronic display, content indicative of the food item information or the therapy information, the processing circuitry is further configured to communicate at least one of a message to a caregiver device or an instruction to a device to deliver a treatment to a patient.

8. The system of claim 1, wherein to generate the therapy information, the processing circuitry is further configured to determine whether the glucose level of the patient is likely to increase or decrease if the food item is consumed.

9. The system of claim 1, wherein the one or more sensors includes a camera configured to capture a two-dimensional image of the object and a LiDAR sensor configured to capture a three-dimensional representation of the object.

10. A method for therapy delivery for diabetes treatment, the method comprising:

capturing, by processing circuitry using one or more sensors, at least one representation of an object;

determining, by the processing circuitry, data corresponding to the at least one representation of the object, wherein the data comprises information identifying the object as a particular food item;

generating, by the processing circuitry, food item information based on the information identifying the object as the particular food item, wherein the food item information comprises at least one of nutrition information or volume information of the particular food item;

determining that the nutrition information or the volume information of the particular food item exceeds a threshold by accessing a food library that defines the threshold;

responsive to determining the nutrition information or the volume information of the particular food item exceeds the threshold, generating, by the processing circuitry, therapy information for a patient based on the food item information and a prediction the patient's glucose level will rise based on the determination the nutrition information or the volume information of the particular food idem exceeds the threshold, wherein generating the therapy information comprises determining at least an insulin type and an insulin dosage based on the food item information;

outputting, by the processing circuitry, content indicative of at least one of the therapy information or the food item information; and automatically administering insulin to the patient in accordance with the insulin type and the insulin dosage, wherein the insulin type comprises at least one of basal insulin or bolus insulin, wherein administration of the insulin to the patient corresponds to the diabetes treatment by causing the glucose level of the patient to lower to within a predetermined range.

11. The method of claim 10, wherein a wearable device may comprise at least one of the one or more sensors, wherein the wearable device is configured to generate at least a portion of the data corresponding to the at least one representation of the object.

12. The method of claim 10, wherein generating the food item information further comprises generating the food item information based on a machine learning model, wherein the machine learning model is trained to map the food item information to feature data corresponding to at least one of a three-dimensional or a two-dimensional representation of the object.

13. The method of claim 10, wherein generating the food item information further comprises generating a mesh model of the object and based on the mesh model, determine which one amongst a plurality of food items corresponds to the object.

14. The method of claim 10, wherein generating the food item information further comprises determining, as part of diabetes therapy for the patient, a treatment amount or type based on the food item information comprising at least one of the nutrition information or the volume information.

15. The method of claim 10, wherein capturing the at least one representation of the object further comprises concurrently capturing a two-dimensional representation using a camera and a three-dimensional representation using a LiDAR sensor.

16. The method of claim 10, wherein outputting the content indicative of the food item information further comprises communicating at least one of a message to a caregiver device or an instruction to a device to deliver a treatment to a patient.

17. The method of claim 10, wherein generating the therapy information further comprises determining whether the glucose level of the patient is likely to increase or decrease if the food item is consumed.

18. A device for therapy delivery for diabetes treatment, the device comprising one or more sensors and one or more processors configured to:
   capture, using the one or more sensors, at least one representation of an object;
   determine data corresponding to the at least one representation of the object, wherein the data comprises information identifying the object as a particular food item;
   generate food item information based on the information identifying the object as the particular food item, wherein the food item information comprises at least one of nutrition information or volume information of the particular food item;
   determine that the nutrition information or the volume information of the particular food item exceeds a threshold by accessing a food library that defines the threshold;
   responsive to determining the nutrition information or the volume information of the particular food idea exceeds the threshold, generate therapy information for a patient based on the food item information and a prediction the patient's glucose level will rise based on the determination the nutrition information or the volume information of the particular food idem exceeds the threshold, wherein generating the therapy information comprises determining at least an insulin type and an insulin dosage based on the food item information;
   output content indicative of at least one of the therapy information or the food item information; and
   automatically deliver insulin to the patient in accordance with the insulin type and the insulin dosage, wherein the insulin type comprises at least one of basal insulin or bolus insulin, wherein administration of the insulin to the patient corresponds to the diabetes treatment by causing the glucose level of the patient to lower to within a predetermined range.

19. The device of claim 18, wherein the one or more sensors comprises a LiDAR sensor and a camera sensor.

* * * * *